United States Patent
Schmid et al.

(10) Patent No.: US 12,188,868 B2
(45) Date of Patent: Jan. 7, 2025

(54) WAVEGUIDE EXCITATION UNIFORMITY

(71) Applicant: Quantum-Si Incorporated, Guilford, CT (US)

(72) Inventors: Gerard Schmid, Guilford, CT (US); Sharath Hosali, Austin, TX (US); James Beach, Austin, TX (US); Kyle Preston, Guilford, CT (US); Ali Kabiri, Guilford, CT (US); Bing Shen, Branford, CT (US)

(73) Assignee: Quantum-Si Incorporated, Branford, CT (US)

( * ) Notice: Subject to any disclaimer, the term of this patent is extended or adjusted under 35 U.S.C. 154(b) by 628 days.

(21) Appl. No.: 17/149,605

(22) Filed: Jan. 14, 2021

(65) Prior Publication Data

US 2021/0215606 A1    Jul. 15, 2021

Related U.S. Application Data

(60) Provisional application No. 62/960,954, filed on Jan. 14, 2020.

(51) Int. Cl.
*G01N 21/64* (2006.01)
*B01L 3/00* (2006.01)
(Continued)

(52) U.S. Cl.
CPC ...... *G01N 21/6428* (2013.01); *B01L 3/50857* (2013.01); *C12Q 1/6816* (2013.01);
(Continued)

(58) Field of Classification Search
None
See application file for complete search history.

(56) References Cited

U.S. PATENT DOCUMENTS 5,961,924 A     10/1999  Reichert et al.
6,787,308 B2     9/2004  Balasubramanian et al.
(Continued)

FOREIGN PATENT DOCUMENTS

JP     2011-017993 A     1/2011
JP     2019-516140 A     6/2019
(Continued)

OTHER PUBLICATIONS

International Search Report and Written Opinion for International Application No. PCT/US2021/013509 dated Apr. 12, 2021.
(Continued)

*Primary Examiner* — Rhonda S Peace
(74) *Attorney, Agent, or Firm* — Wolf, Greenfield & Sacks, P.C.

(57) ABSTRACT

Systems and methods for optical power distribution within an integrated device, in a substantially uniform manner, to a large number of sample wells and/or other photonic elements. The integrated device and related instruments and systems may be used to analyze samples in parallel. The integrated device may include a grating coupler configured to receive light from an excitation source and optically couple with multiple waveguides configured to couple with sample wells. Vertical extents of optical modes of individual waveguides may be modulated to adjust confinement of light within the waveguides. This modulation may enable more uniform distribution of excitation light to the sample wells, improve excitation efficiency, and prevent overpower on regions of the integrated device.

24 Claims, 17 Drawing Sheets

(51) Int. Cl.
*C12Q 1/6816* (2018.01)
*G02B 6/122* (2006.01)
*G02B 6/14* (2006.01)

(52) U.S. Cl.
CPC ............ *G02B 6/1228* (2013.01); *G02B 6/14* (2013.01); *B01L 2300/0654* (2013.01); *B01L 2300/0829* (2013.01)

(56) References Cited

U.S. PATENT DOCUMENTS

| | | | |
|---|---|---|---|
| 6,917,726 B2 | 7/2005 | Levene et al. | |
| 7,175,811 B2 | 2/2007 | Bach et al. | |
| 7,426,322 B2 | 9/2008 | Hyde | |
| 7,738,086 B2 | 6/2010 | Shepard et al. | |
| 7,820,983 B2 | 10/2010 | Lundquist et al. | |
| 7,834,329 B2 | 11/2010 | Lundquist et al. | |
| 7,838,847 B2 | 11/2010 | Lundquist et al. | |
| 8,053,742 B2 | 11/2011 | Lundquist et al. | |
| 8,207,509 B2 | 6/2012 | Lundquist et al. | |
| 8,274,040 B2 | 9/2012 | Zhong et al. | |
| 8,278,728 B2 | 10/2012 | Murshid | |
| 8,465,699 B2 | 6/2013 | Fehr et al. | |
| 8,471,219 B2 | 6/2013 | Lundquist et al. | |
| 8,471,230 B2 | 6/2013 | Zhong et al. | |
| 8,502,169 B2 | 8/2013 | Rigneault et al. | |
| 8,618,507 B1 | 12/2013 | Lundquist et al. | |
| 9,029,802 B2 | 5/2015 | Lundquist et al. | |
| 9,157,864 B2 | 10/2015 | Fehr et al. | |
| 9,222,123 B2 | 12/2015 | Zhong et al. | |
| 9,222,133 B2 | 12/2015 | Lundquist et al. | |
| 9,223,084 B2 | 12/2015 | Grot et al. | |
| 9,372,308 B1 | 6/2016 | Saxena et al. | |
| 9,587,276 B2 | 3/2017 | Lundquist et al. | |
| 9,606,060 B2 | 3/2017 | Chen et al. | |
| 9,658,161 B2 | 5/2017 | Saxena et al. | |
| 9,666,748 B2 | 5/2017 | Leobandung | |
| 9,719,138 B2 | 8/2017 | Zhong et al. | |
| 9,765,395 B2 | 9/2017 | Goldsmith | |
| 9,946,017 B2 | 4/2018 | Saxena et al. | |
| 10,018,764 B2 | 7/2018 | Grot et al. | |
| 10,090,429 B2 | 10/2018 | Leobandung | |
| 10,138,515 B2 | 11/2018 | Fehr et al. | |
| 10,280,457 B2 | 5/2019 | Zhong et al. | |
| 10,310,178 B2 | 6/2019 | Saxena et al. | |
| 10,487,356 B2 | 11/2019 | Lundquist et al. | |
| 10,578,788 B2 | 3/2020 | Grot et al. | |
| 10,655,172 B2 | 5/2020 | Rank et al. | |
| 10,724,090 B2 | 7/2020 | McCaffrey et al. | |
| 11,072,827 B2* | 7/2021 | Chen | B01L 3/50857 |
| 11,344,200 B2* | 5/2022 | Rothberg | A61B 5/0071 |
| 11,347,002 B2* | 5/2022 | Konegawa | G02B 6/4202 |
| 2002/0182716 A1 | 12/2002 | Weisbuch et al. | |
| 2003/0174992 A1 | 9/2003 | Levene et al. | |
| 2010/0065726 A1 | 3/2010 | Zhong et al. | |
| 2013/0116153 A1 | 5/2013 | Bowen et al. | |
| 2015/0192735 A1* | 7/2015 | Ellis-Monaghan | G02B 6/125 427/163.2 |
| 2017/0146479 A1 | 5/2017 | Levine et al. | |
| 2017/0235047 A1* | 8/2017 | Kitazoe | G02B 6/122 385/131 |
| 2017/0350818 A1 | 12/2017 | Rothberg et al. | |
| 2019/0025511 A1 | 1/2019 | Rothberg et al. | |
| 2019/0292590 A1 | 9/2019 | Zhong et al. | |
| 2021/0215606 A1* | 7/2021 | Schmid | G02B 6/1228 |

FOREIGN PATENT DOCUMENTS

| | | |
|---|---|---|
| WO | WO 2011/153962 A1 | 12/2011 |
| WO | WO 2016/021505 A1 | 2/2016 |
| WO | WO 2019/039325 A1 | 2/2019 |

OTHER PUBLICATIONS

Hale, Fibre Optic Sensors using Adiabatically Tapered Single Mode Fibres. Dissertation submitted to the University of Cambridge. Feb. 1994. 209 pages.

Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.

Taitt et al., Evanescent wave fluorescence biosensors. Biosens Bioelectron. Jun. 2005;20(12):2470-87. Epub Dec. 8, 2004.

International Preliminary Report on Patentability for International Application No. PCT/US2021/013509 mailed Jul. 28, 2022.

* cited by examiner

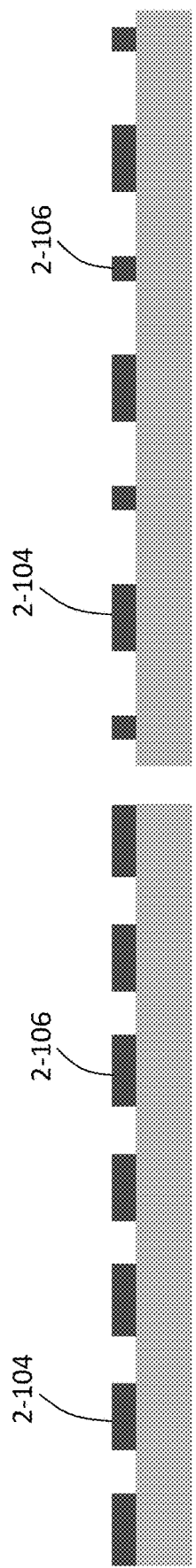
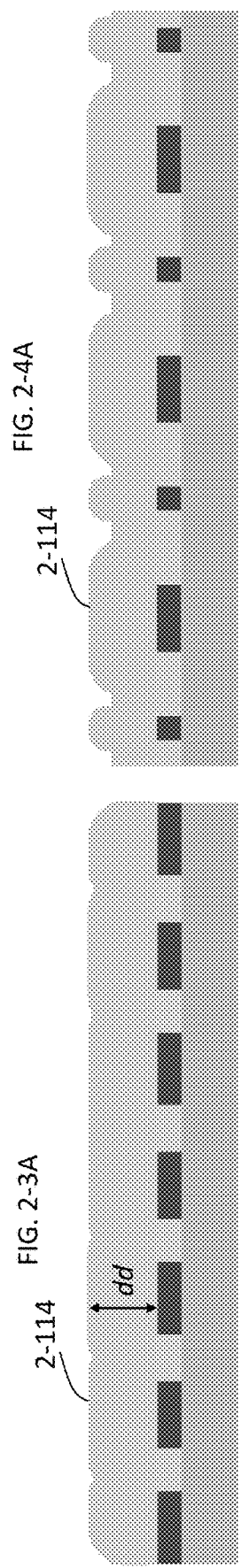
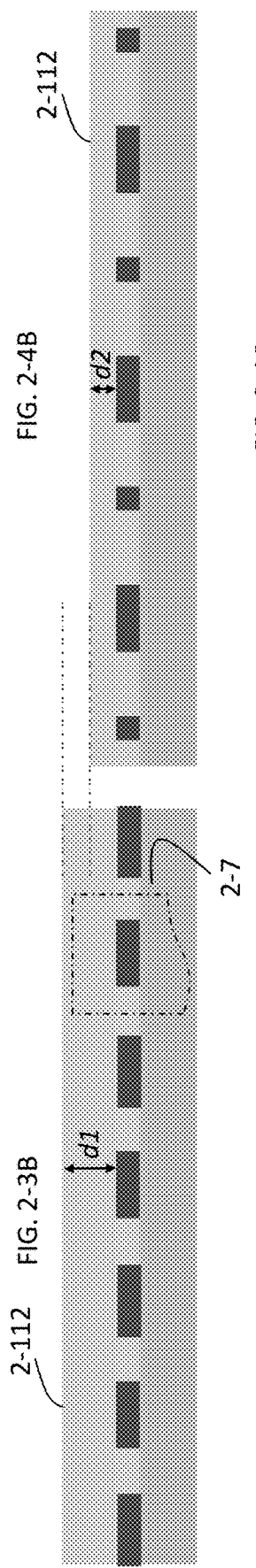
FIG. 2-3A
FIG. 2-3B
FIG. 2-3C
FIG. 2-4A
FIG. 2-4B
FIG. 2-4C

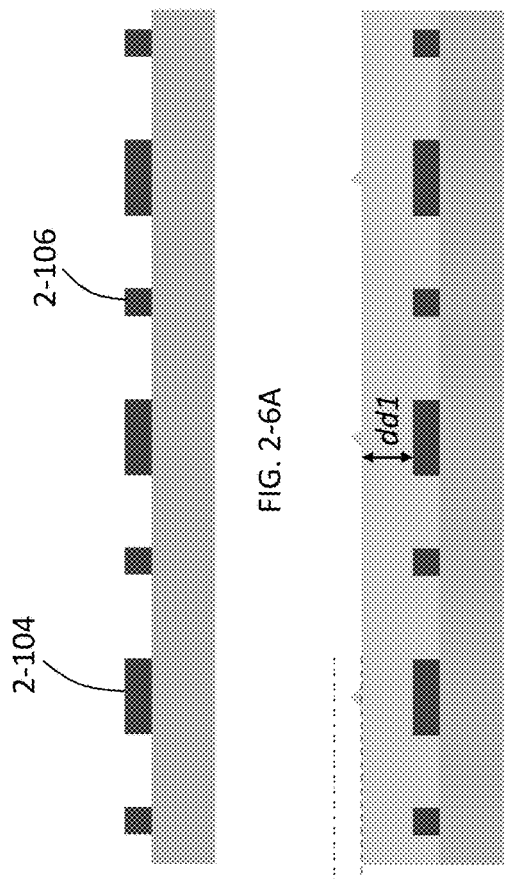
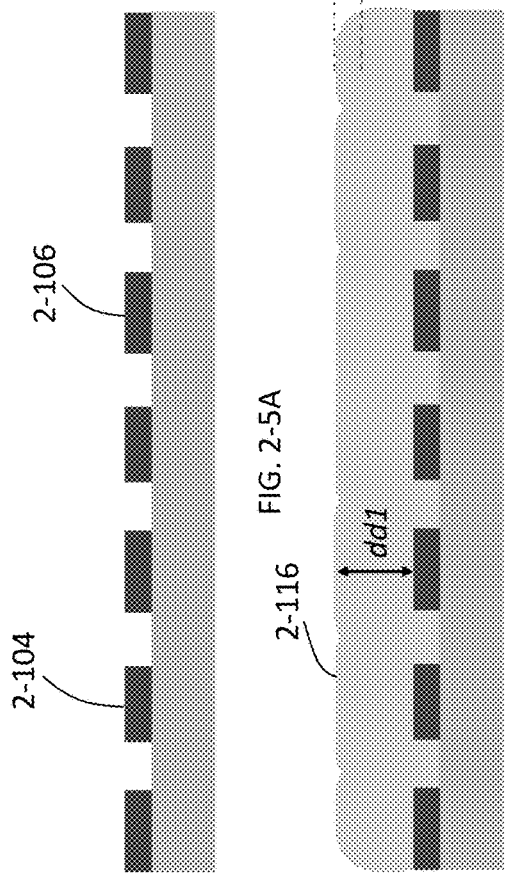

WAVEGUIDE EXCITATION UNIFORMITY

RELATED APPLICATION

This application claims the benefit under 35 U.S.C. § 119(e) of U.S. Provisional Application Ser. No. 62/960,954, filed Jan. 14, 2020 and titled "WAVEGUIDE EXCITATION UNIFORMITY," which is hereby incorporated herein by reference in its entirety.

FIELD OF THE APPLICATION

The present application is directed generally to devices, methods, and techniques for coupling optical energy into an integrated device and distributing optical energy to multiple regions of the device. The integrated device may be used for performing parallel, quantitative analysis of biological and/or chemical samples, including for nucleic acid sequencing and protein sequencing.

BACKGROUND

Instruments that are capable of massively-parallel analyses of biological or chemical samples are typically limited to laboratory settings because of several factors that can include their large size, lack of portability, requirement of a skilled technician to operate the instrument, power demands, need for a controlled operating environment, and cost. Moreover, some analysis of biological or chemical samples is performed in bulk such that a large amount of a particular type of sample is necessary for detection and quantitation.

Analysis of biological or chemical samples may involve tagging samples with luminescent markers that emit light of a particular wavelength, illuminating with a light source the tagged samples, and detecting the luminescent light with a photodetector. Such techniques conventionally involve expensive laser light sources and systems to illuminate the tagged samples as well as complex detection optics and electronics to collect the luminescence from the tagged samples.

SUMMARY

Some embodiments are directed to a system including an array of reaction chambers and a waveguide that delivers excitation light to at least a portion of the reaction chambers, wherein a vertical extent of an optical mode of the waveguide is modulated to adjust confinement of light within the waveguide.

In some embodiments, the vertical extent of the optical mode is modulated by changing a thickness of a waveguide core layer along the length of the waveguide.

In some embodiments, the vertical extent of the optical mode is modulated by changing a refractive index of a waveguide core or cladding material along the length of the waveguide.

In some embodiments, the thickness of the waveguide core layer along the length of the waveguide is changed by transferring a topography of a photoresist layer.

In some embodiments, the system comprises a plurality of waveguides having uniform widths; and a plurality of dummy structures having tapered widths, wherein the plurality of waveguides and the plurality of dummy structures are disposed alternatively.

In some embodiments, the plurality of waveguides and the plurality of dummy structures are in a waveguide core layer.

Some embodiments are directed to a system including an array of reaction chambers and a waveguide that delivers excitation light to at least a portion of the reaction chambers, wherein a distance between the waveguide and the reaction chambers is modulated to compensate for waveguide losses.

In some embodiments, a thickness of a cladding layer of the waveguide is controlled to modulate the distance between the waveguide and the reaction chambers.

In some embodiments, the system comprises a plurality of waveguides having uniform widths; and a plurality of dummy structures having tapered widths, wherein the plurality of waveguides and the plurality of dummy structures are disposed alternatively.

In some embodiments, the system comprises a plurality of waveguides having tapered widths; and a plurality of dummy structures having tapered widths, wherein the plurality of waveguides and the plurality of dummy structures are disposed alternatively.

In some embodiments, the system comprises a plurality of waveguides having tapered widths in a first direction; and a plurality of dummy structures having tapered widths in a second direction opposite to the first direction, wherein the plurality of waveguides and the plurality of dummy structures are disposed alternatively.

Some embodiments are directed to a method comprising providing a waveguide to deliver excitation light to an array of reaction chambers and modulating a vertical extent of an optical mode of the waveguide to adjust confinement of light within the waveguide.

In some embodiments, the modulating includes changing a thickness of a waveguide core layer along the length of the waveguide.

In some embodiments, the modulating includes changing a refractive index of a waveguide core or cladding material.

Some embodiments are directed to a method comprising providing a waveguide to deliver excitation light to an array of reaction chambers and modulating a distance between the waveguide and reaction chambers.

In some embodiments, the modulating includes controlling a thickness of a cladding layer of the waveguide.

In some embodiments, controlling the thickness of the cladding layer of the waveguide includes providing the cladding layer with a tapered thickness by planarizing a material for the cladding layer on a modulated waveguide pattern.

In some embodiments, controlling the thickness of the cladding layer of the waveguide includes providing the cladding layer with a tapered thickness by depositing a material for the cladding layer on a modulated waveguide pattern.

In some embodiments, controlling the thickness of the cladding layer of the waveguide includes providing the cladding layer with a tapered thickness by transferring a topography of a photoresist layer to the cladding layer.

Some embodiments are directed to a method comprising forming an array of reaction chambers; forming a waveguide to deliver excitation light to the reaction chambers; and modulating the waveguide to deliver as close to an equal amount of excitation light to each reaction chamber.

In some embodiments, the modulating includes modulating a vertical extent of the optical mode of the waveguide.

In some embodiments, the modulating includes modulating a thickness along its length of the waveguide.

In some embodiments, the modulating includes modulating a distance along its length of the waveguide from each reaction chamber.

Some embodiments are directed to a method comprising exciting with excitation light delivered through a waveguide a sample within each of a plurality of reaction chambers, wherein the waveguide is modulated such that a substantially same amount of light is delivered to each reaction chamber.

The foregoing summary is provided by way of illustration and is not intended to be limiting.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 1-2 is a planar schematic of an integrated device, according to some embodiments.

FIG. 2-1 is a planar schematic of a waveguide array, showing sample wells, waveguides, and dummy structures, according to some embodiments.

FIG. 2-2 is a cross-sectional view of the waveguide array of FIG. 2-1 along a line marked "2-2", illustrating a waveguide cladding layer with a modulated thickness along the length of a waveguide, according to some embodiments.

FIGS. 2-3A-2-3C are cross-sectional views of the waveguide array of FIG. 2-1 along a line marked "2-3", illustrating a first method for fabricating the waveguide array, according to some embodiments.

FIGS. 2-4A-2-4C are cross-sectional views of the waveguide array of FIG. 2-1 along a line marked "2-4", illustrating the first method for fabricating the waveguide array, according to some embodiments.

FIGS. 2-5A-2-5B are cross-sectional views of the waveguide array of FIG. 2-1 along the line marked "2-3", illustrating a second method for fabricating the waveguide array, according to some embodiments.

FIGS. 2-6A-2-6B are cross-sectional views of the waveguide array of FIG. 2-1 along the line marked "2-4", illustrating the second method for fabricating the waveguide array, according to some embodiments.

FIG. 2-7A is an enlarged view of a region marked "2-7" in FIG. 2-3C, according to some embodiments.

FIG. 2-7B is a schematic illustrating field intensity of an optical mode within and near the waveguide of FIG. 2-7A, according to some embodiments.

FIG. 2-8 is a planar schematic of a waveguide array with an alternative layout for sample wells, according to some embodiments.

FIG. 3-1 is a planar schematic of a waveguide array, showing sample wells, waveguides, and dummy structures, according to some embodiments.

FIG. 4-1 is a planar schematic of a waveguide array, showing sample wells, waveguides, and dummy structures, according to some embodiments.

FIGS. 4-2A-4-2B are cross-sectional views of the waveguide array of FIG. 4-1 along the line marked "4-2", illustrating a method for fabricating the waveguide array, according to some embodiments.

FIG. 5-1A is a block diagram of an integrated device and an instrument, according to some embodiments.

FIG. 5-1B is a schematic of an apparatus including an integrated device, according to some embodiments.

FIG. 5-2 is a schematic of a pixel having a sample well, optical waveguide, and time-binning photodetector, according to some embodiments.

FIG. 5-3 is a schematic of an exemplary biological reaction that may occur within a sample well, according to some embodiments.

FIG. 5-4 is a plot of emission probability curves for two different fluorophores having different decay characteristics.

FIG. 5-5 is a plot of time-binning detection of fluorescent emission, according to some embodiments.

FIG. 5-6 is an exemplary time-binning photodetector, according to some embodiments.

FIG. 5-7A is a schematic illustrating pulsed excitation and time-binned detection of fluorescent emission from a sample, according to some embodiments.

FIG. 5-7B is a histogram of accumulated fluorescent photon counts in various time bins after repeated pulsed excitation of a sample, according to some embodiments.

FIGS. 5-8A-5-8D are different histograms that may correspond to the four nucleotides (T, A, C, G) or nucleotide analogs, according to some embodiments.

DETAILED DESCRIPTION

I. Introduction

Figure 1:
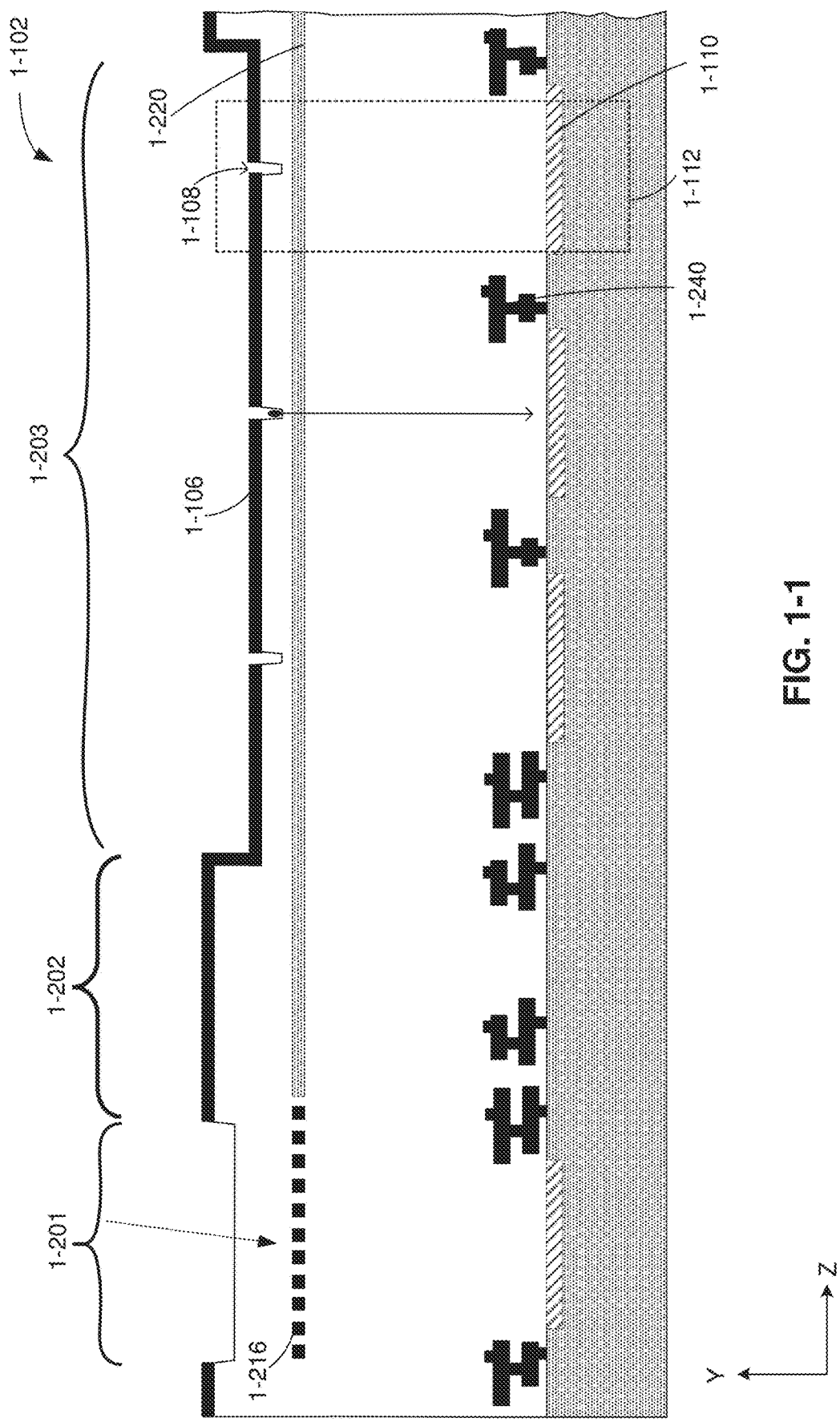
FIG. 1-1 is a cross-sectional schematic of an integrated device, according to some embodiments.

Aspects of the present application relate to integrated devices, instruments and related systems capable of analyzing samples in parallel, including identification of single molecules and nucleic acid sequencing. Such an instrument may be compact, easy to carry, and easy to operate, allowing a physician or other provider to readily use the instrument and transport the instrument to a desired location where care may be needed. Analysis of a sample may include labeling the sample with one or more fluorescent markers, which may be used to detect the sample and/or identify single molecules of the sample (e.g., individual nucleotide identification as part of nucleic acid sequencing). A fluorescent marker may become excited in response to illuminating the fluorescent marker with excitation light (e.g., light having a characteristic wavelength that may excite the fluorescent marker to an excited state) and, if the fluorescent marker becomes excited, emit emission light (e.g., light having a characteristic wavelength emitted by the fluorescent marker by returning to a ground state from an excited state). Detection of the emission light may allow for identification of the fluorescent marker, and thus, the sample or a molecule of the sample labeled by the fluorescent marker. According to some embodiments, the instrument may be capable of massively-parallel sample analyses and may be configured to handle tens of thousands of samples or more simultaneously.

The inventors have recognized and appreciated that an integrated device, having sample wells [also referred to as reaction chambers] configured to receive the sample and integrated optics formed on the integrated device, and an instrument configured to interface with the integrated device may be used to achieve analysis of this number of samples. The instrument may include one or more excitation light sources, and the integrated device may interface with the instrument such that the excitation light is delivered to the sample wells using integrated optical components (e.g., waveguides, optical couplers, optical splitters) formed on the integrated device. The optical components may improve the uniformity of illumination across the sample wells of the integrated device and may reduce a large number of external optical components that might otherwise be needed. Furthermore, the inventors have recognized and appreciated that integrating photodetectors on the integrated device may improve detection efficiency of fluorescent emissions from the sample wells and reduce the number of light-collection components that might otherwise be needed.

According to some embodiments, the integrated device has an array of sample wells, which allow for multiplexed analysis of multiple samples across the array, and an optical system configured to deliver excitation light to the array of sample wells. Performance of the integrated device may depend on the ability of the integrated device to deliver excitation light across the array of sample wells using the optical system. Additionally, performance of the integrated device may relate to the ability of the optical system to deliver excitation light to individual sample wells in a substantially uniform manner, such as by delivering a relatively constant intensity or electric field strength to individual sample wells. Specifically, performance related factors related to the optical system may include optical loss arising from scattering and/or absorption by the sample wells, the coupling efficiency of an optical coupler (e.g., a grating coupler configured to receive light from an external light source), optical loss arising from splitting excitation light among multiple waveguides, and coupling efficiency of individual waveguides with multiple sample wells.

To increase the multiplexing capabilities of the integrated device, it can be desirable to increase the number of sample wells in the array to allow for the ability to analyze more samples at any particular time while using the integrated device. As the integrated device is scaled by increasing the number of sample wells, challenges in performance of the integrated device may arise because of one or more of these factors. For example, a row of sample wells may receive light by coupling to a waveguide of the optical system such that as light propagates along the waveguide, the sample wells in the row receive a portion of the light. Optical loss may arise from the individual sample wells scattering and/or absorbing the light, which may cumulatively result in the last sample well in the row (e.g., distal from the optical input end of the waveguide) receiving a lower intensity or electric field strength than the first sample well in the row (e.g., the sample well proximate to the optical input end of the waveguide). Such optical loss may impact the signal-to-noise ratio of the measurements conducted by using the integrated device. As more sample wells are added to an array, these optical losses may lead to further reduction in signal-to-noise ratio, which can impact the quality and reliability of the analysis conducted.

Accordingly, aspects of the present application relate to optical components and particular arrangements to include in an optical system of the integrated device that may allow for improved distribution of light among an array of sample wells. These optical components and arrangements may allow for delivering light in a substantially uniform manner such that individual sample wells, including sample wells within the same row, receive a similar intensity and/or electric field strength. The optical components and arrangements described herein may allow for the implementation of integrated devices having a larger number of sample wells in the array, as well as a desired performance in analyzing samples across the array.

Additional considerations as part of scaling up the number of sample wells in the array may include fabrication costs and constraints. Accordingly, aspects of the present application relate to optical components and systems that take into account fabrication costs and constraints (e.g., by reducing the number or complexity of the fabrication steps) while allowing for the resulting integrated device to achieve a desired optical performance.

Some aspects of the present application relate to waveguide configurations that may allow for illuminating a large number of sample wells and/or other photonic elements, in a substantially uniform manner.

In particular, some aspects are directed to modulating a vertical extent of an optical mode of a waveguide to adjust confinement of light within, and along the length of, the waveguide. This modulation may compensate for optical losses. This modulation enables more uniform distribution of excitation light to the sample wells, improve excitation efficiency, and prevent overpower on regions of the integrated device. The modulation may be accomplished by changing a thickness and/or width of the waveguide, changing a refractive index of the waveguide and/or a refractive index of the waveguide's cladding material, or any suitable combinations of the techniques described herein.

Other aspects are directed to modulating a distance between a waveguide and sample wells to compensate for optical losses. This modulation of the distance may be carried out by controlling a thickness of a cladding layer of the waveguide. Accordingly, aspects of the present application relate to techniques for controlling the thickness of the cladding layer of the waveguide along the length of the waveguide. In some embodiments, the techniques may include modulating a waveguide pattern density. In some embodiments, the techniques may include modulating the topography of the cladding layer. In some embodiments, the techniques may include modulating the lateral positions of the sample wells relative to a waveguide. In some embodiments, the techniques may be used alone or in any suitable combination.

Additional systems and methods for delivering uniform excitation light to an array of sample wells are described in U.S. patent application Ser. No. 16/733,296 titled "OPTICAL WAVEGUIDES AND COUPLERS FOR DELIVERING LIGHT TO AN ARRAY OF PHOTONIC ELEMENTS," which is herein incorporated by reference in its entirety.

While the techniques for an optical system as described in the present application are discussed in connection with delivering excitation light to an array of sample wells, it should be appreciated that one or more of these techniques may be used, alone or in combination, in other contexts that involve distributing light to an array of photonic elements within an integrated device. For example, the techniques of the present application may be implemented in an array of optical components, such as an array of sensors. In other words, rather than, or in addition to, providing techniques to deliver uniform excitation light to an array of sample wells, techniques can be employed to address non-uniformities in excitation light delivery within optical components used to deliver or receive emission light from excited samples within the sample wells. Additionally, it should be appreciated that the techniques described herein are not limited to the context of analyzing biological or chemical samples, but rather may be implemented in applications where it is desired to distribute light among many photonic elements in substantially uniform manner.

The aspects and embodiments described above, as well as additional aspects and embodiments, are described further below. These aspects and/or embodiments may be used individually, all together, or in any combination of two or more, as the application is not limited in this respect.

II. Integrated Device

A. Overview

A cross-sectional schematic of integrated device 1-102 illustrating a row of pixels 1-112 is shown in FIG. 1-1. Integrated device 1-102 may include coupling region 1-201, routing region 1-202, and pixel region 1-203. As discussed herein, an optical system of the integrated device may include different types of optical components, which may be located within regions 1-201, 1-202, and 1-203 of the integrated device. Coupling region 1-201 may include grating coupler 1-216, which may be configured to receive excitation light (shown in the dashed line) and propagate the excitation light to one or more optical components in routing region 1-202. Routing region 1-202 may include an optical routing network configured to split light among multiple waveguides 1-220 configured to propagate light to pixel region 1-203. Pixel region 1-203 may include a plurality of pixels 1-112 having sample wells 1-108 positioned on a surface at a location separate from coupling region 1-201, which is where excitation light (shown as the dashed arrow) couples to integrated device 1-102. Sample wells 1-108 may be formed through metal layer(s) 1-106. One pixel 1-112, illustrated by the dotted rectangle, is a region of integrated device 1-102 that includes a sample well 1-108 and photodetector region having one or more photodetectors 1-110.

FIG. 1-1 illustrates the path of excitation (shown in dashed lines) by coupling a beam of excitation light to coupling region 1-201 and to sample wells 1-108. The row of sample wells 1-108 shown in FIG. 1-1 may be positioned to optically couple with waveguide 1-220. Excitation light may illuminate a sample located within a sample well. The sample may reach an excited state in response to being illuminated by the excitation light. When a sample is in an excited state, the sample may emit emission light, which may be detected by one or more photodetectors associated with the sample well. FIG. 1-1 schematically illustrates the path of emission light (shown as the solid line) from a sample well 1-108 to photodetector(s) 1-110 of pixel 1-112. The photodetector(s) 1-110 of pixel 1-112 may be configured and positioned to detect emission light from sample well 1-108. Examples of suitable photodetectors are described in U.S. patent application Ser. No. 14/821,656 titled "INTEGRATED DEVICE FOR TEMPORAL BINNING OF RECEIVED PHOTONS," which is incorporated by reference in its entirety. Additional examples of suitable photodetectors are described in U.S. patent application Ser. No. 15/852,571, titled "INTEGRATED PHOTODETECTOR WITH DIRECT BINNING PIXEL," which is incorporated herein by reference in its entirety. For an individual pixel 1-112, a sample well 1-108 and its respective photodetector(s) 1-110 may be aligned along a common axis (along the y-direction shown in FIG. 1-1). In this manner, the photodetector(s) may overlap with the sample well within a pixel 1-112.

Figures 1, 2:
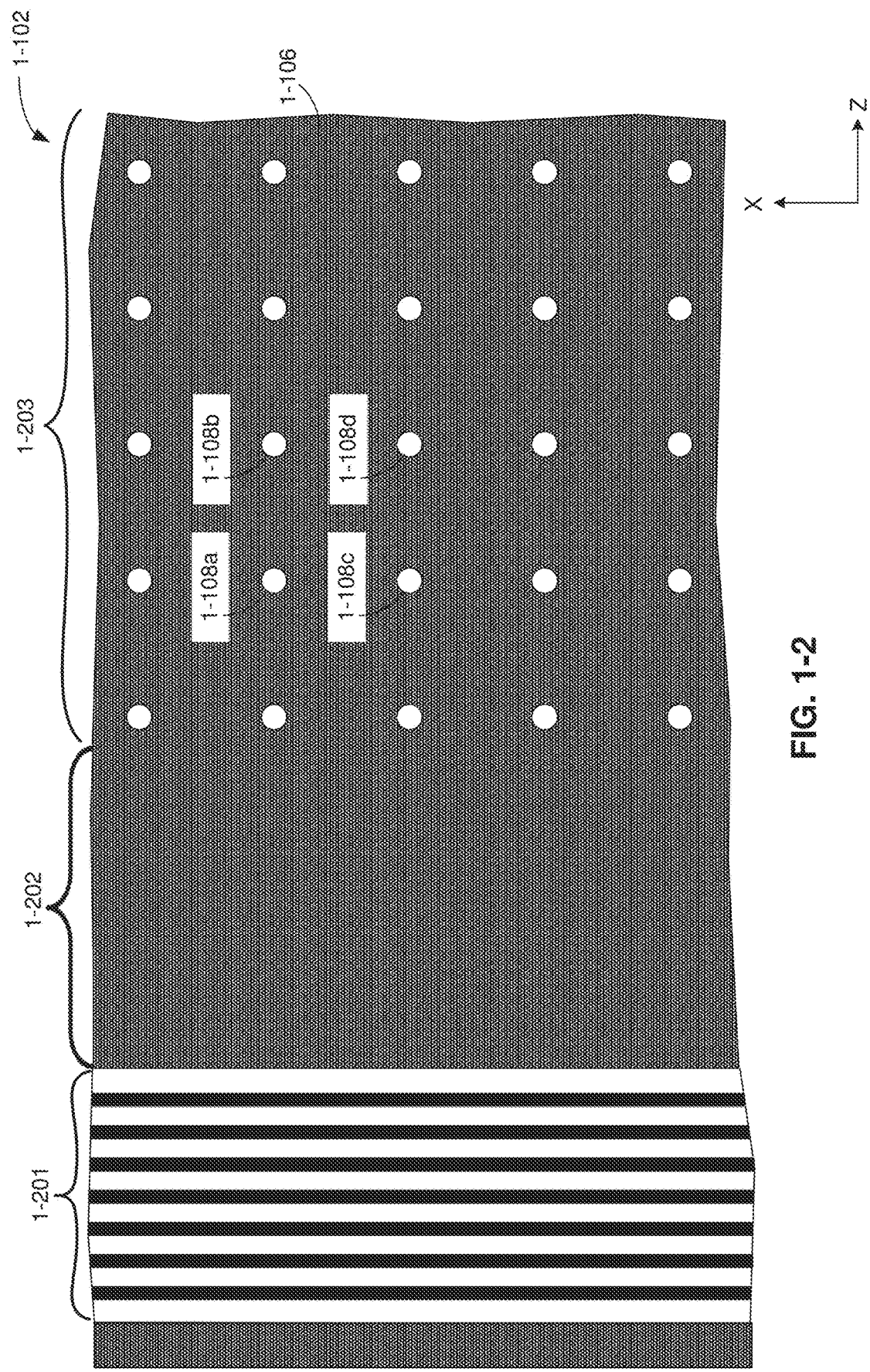

A planar view of integrated device 1-102 illustrating five rows of pixels is shown in FIG. 1-2. As shown in FIG. 1-2, sample well 1-108a and sample well 1-108b are in the same row and sample well 1-108c and 1-108d are in the same row. Aspects of the present application relate to techniques for receiving excitation light incident to coupling region 1-201 and propagating excitation light to the array of sample wells 1-108. These techniques may include having one or more optical grating couplers positioned in coupling region 1-201 and waveguide architecture, positioned in routing region 1-202 and/or pixel region 1-203, for delivering excitation light from the coupling region 1-201 to the individual sample wells 1-108.

B. Waveguide Architecture

Some embodiments relate to waveguides configured to substantially uniformly couple excitation energy generated by an excitation source to individual samples in sample wells through, for example, evanescent coupling. In some embodiments, sample wells may be disposed in an array having rows and columns, and individual waveguides may be configured to deliver excitation energy to sample wells in corresponding rows or columns. In some embodiments, the waveguides may be configured to substantially uniformly provide (e.g., with a variation in intensity that is less than 50%; in some embodiments, less than 20%; in some embodiments, less than 10%) excitation energy among the sample wells in a row or column and/or in multiple rows or columns. In some embodiments, the number of sample wells along a waveguide may be larger than 500, for example, in the range of 500 to 5000.

The waveguides may be configured to compensate for optical losses. Optical losses may cause nonuniform excitation within an array, and/or result in suboptimal excitation efficiencies, which may be referred to as the number of measurements enabled by an optical power. Without compensation, the power in a waveguide may decrease, for example, exponentially with respect to the distance it traverses across a waveguide array. Embodiments of the waveguides are configured to improve excitation uniformity and excitation efficiency across large arrays of sample wells, and to prevent overpower on regions of an integrated device comprising large arrays of sample wells.

Vertical extents of optical modes of individual waveguides may be modulated to adjust confinement of light within, and along the length of, the waveguides. In some embodiments, the thicknesses and/or widths of individual waveguides may be modulated along the lengths of individual waveguides. In some embodiments, the refractive index of the waveguides and/or the refractive index of its cladding material may be modulated.

In some embodiments, the distances between a waveguide and respective sample wells may be modulated to adjust the excitation of sample wells along the waveguide. In some embodiments, the distances between a waveguide and respective sample wells may be modulated by modulating the thickness of a waveguide cladding layer along the length of the waveguide. In some embodiments, the distances between a waveguide and respective sample wells may be modulated by modulating the lateral position of the sample wells with respect to the waveguide along the length of the waveguide. For example, the sample wells may be disposed such that, along the length of a waveguide, sample wells closer in distance to an excitation source are offset more from the waveguide than sample wells farther away from the excitation source. The offset may be in a direction perpendicular to the direction that the waveguide extends (for example, as illustrated in FIG. 2-8). In some embodiments, the techniques described herein may be used alone or in any suitable combination.

In some embodiments, a thickness profile of a cladding layer on top of an array of waveguides may be modulated. FIG. 2-1 illustrates a planar schematic of a waveguide array 2-100, according to some embodiments. The waveguide array 2-100 may extend from an array beginning end 2-108 to an array ending end 2-110. The array beginning end 2-108 may be closer in distance to an excitation source than the array ending end 2-110. The waveguide array 2-100 may include waveguides 2-104 and dummy structures 2-106 disposed in between adjacent waveguides 2-104. Waveguides 2-104 and dummy structures 2-106 may be in a waveguide core layer. For example, a waveguide core layer may be deposited on a substrate and patterned into waveguides and dummy structures. Sample wells 2-102 may be disposed on top of the waveguides 2-104. There may be no sample wells disposed on top of the dummy structures 2-106. Such configuration may allow the dimensions (e.g., width) of the dummy structures 2-106 adapted according to the needs of subsequent fabrication processes, while the dimensions of the waveguides 2-104 adapted for modulating vertical extents of optical modes of the waveguides to adjust confinement of light within, and along the lengths of, the waveguides. For example, the results of some subsequent fabrication processes such as chemical mechanical polishing (CMP) and high density plasma chemical vapor deposition (HDP) may depend on the pattern density of an underlying layer. The addition of the dummy structures may allow the modulation of the pattern density of a photolithography mask designed for the waveguides 2-104 to achieve a desired pattern density for the subsequent fabrication processes, by modulating the dimensions of the dummy structures 2-106 and without changing the dimensions of the waveguides 2-104 that are adapted for modulated vertical extents of optical modes.

The waveguide array 2-100 may have a modulated pattern density. The pattern density may be configured to decrease as the distance to the excitation source increase. In the illustrated example, the waveguides 2-104 have constant widths along the lengths of the waveguides, which may be configured to maintain a steep decay rate of the evanescent field. In the illustrated example, the dummy structures 2-106 have tapered widths along the length of the dummy structures, which causes, from the array beginning end 2-108 to the array ending end 2-110, a decrease of the waveguide pattern density.

Distances between the waveguides 2-104 and sample wells 2-102 may be modulated based, at least in part, on the modulated waveguide pattern density. The distances between a waveguide 2-104 and a row of sample wells 2-102 on top of the waveguide may be configured to decrease as the waveguide extends away from the excitation source. FIG. 2-2 illustrates a cross-sectional view of the waveguide array 2-100 along a line marked "2-2" in FIG. 2-1, according to some embodiments. A cladding layer 2-112 may be formed on top of the waveguide 2-104. A thickness de of the cladding layer 2-112 may be modulated along the length of the waveguide 2-104. As illustrated, the thickness de of the cladding layer 2-112 gradually tapers from the array beginning end 2-108 to the array ending end 2-110. Sample wells 2-102 may be formed in the cladding layer 2-112 by, for example, photolithography and etching. As the depths dw of the sample wells 2-102 may be substantially constant for defining the locations of the sample, distances between the sample wells 2-102 and the waveguide 2-104 may therefore decrease along the length of the waveguide 2-104. The reduced sample-to-waveguide distance can compensate for the loss of power in the waveguide as the excitation energy traverses across the waveguide and away from the excitation source, and enable a substantially similar amount of light to interact with samples in the sample wells along the length of the waveguide and/or across different regions of the waveguide array.

In some embodiments, the waveguide array 2-100 may be fabricated with a first method illustrated in FIG. 2-3A-2-4C.

FIGS. 2-3A-2-3C illustrate cross-sectional views of the waveguide array 2-100 along a line near the array beginning end 2-108 and marked "2-3" in FIG. 2-1, according to some embodiments. FIGS. 2-4A-2-4C illustrate cross-sectional views of the waveguide array 2-100 along a line near the array ending end 2-110 and marked "2-4" in FIG. 2-1, according to some embodiments.

In the fabrication step illustrated in FIG. 2-3A and FIG. 2-4A, waveguides 2-104 and dummy structures 2-106 may be fabricated by depositing a layer of waveguide core material on a substrate and patterning the layer of waveguide core material by lithography and etching.

In the fabrication step illustrated in FIG. 2-3B and FIG. 2-4B, a cladding layer 2-114 may be deposited on top of the patterned layer of waveguide core material using a deposition process substantially independent of the underlying pattern density, for example, plasma enhanced chemical vapor deposition (PECVD). As illustrated, the thickness dd of the deposited cladding layer 2-114 may be substantially constant from the array beginning end 2-108 to the array ending end 2-110.

In the fabrication step illustrated in FIG. 2-3C and FIG. 2-4C, the cladding layer 2-112 may be formed by polishing/planarizing the deposited cladding layer 2-114 using, for example, a chemical mechanical polishing (CMP) process. The CMP process may be configured such that a region that has lower waveguide pattern density is polished faster than a region that has higher waveguide pattern density. As illustrated, the thickness d1 of the cladding layer 2-112 at the array beginning end 2-108 is larger than the thickness d2 of the cladding layer 2-112 at the array ending end 2-110.

In some embodiments, the waveguide array 2-100 may be fabricated with a second method illustrated in FIGS. 2-5A-2-6B. FIGS. 2-5A-2-5B illustrate cross-sectional views of the waveguide array 2-100 along the line near the array beginning end 2-108 and marked "2-3" in FIG. 2-1, according to some embodiments. FIGS. 2-6A-2-6B illustrate cross-sectional views array 2-100 along a line near the array beginning end 2-108 and marked "2-4" in FIG. 2-1, according to some embodiments.

Similar to the fabrication step illustrated in FIG. 2-3A and FIG. 2-4A, in the fabrication step illustrated in FIG. 2-5A and FIG. 2-6A, the waveguides 2-104 and dummy structures 2-106 may be fabricated by depositing a layer of waveguide core material on the substrate and patterning the layer of waveguide core material by lithography and etching.

Different from the fabrication step illustrated in FIG. 2-3B and FIG. 2-4B, in the fabrication step illustrated in FIG. 2-5B and FIG. 2-6B, a cladding layer 2-116 may be deposited on top of the patterned layer of waveguide core material using a deposition process dependent on the underlying pattern density, for example, high density plasma chemical vapor deposition (HDP). As illustrated, the thickness dd1 of the deposited cladding layer 2-116 at the array beginning end 2-108 is larger than the thickness dd2 of the deposited cladding layer 2-116 at the array ending end 2-110.

After the fabrication step illustrated in FIG. 2-5B and FIG. 2-6B, similar to the fabrication step illustrated in FIG. 2-3C and FIG. 2-4C, the cladding layer 2-112 may be formed by polishing/planarizing the deposited cladding layer 2-116 using, for example, CMP process. The thickness profile of the deposited cladding layer 2-116 may be maintained or enhanced when it is transferred to the cladding layer 2-112 by the polishing/planarizing process.

The vertical extent of the optical mode of a waveguide may be modulated by a tapered cladding layer (e.g., the cladding layer 2-112 shown in FIG. 2-2). FIG. 2-7A is an enlarged view of a region marked "2-7" in FIG. 2-3C, according to some embodiments. FIG. 2-7B is a simulated schematic illustrating field intensity of an optical mode within and near a waveguide 2-104, according to some embodiments. The field intensity of the optical mode of the waveguide 2-104 may depend on the width w and thickness t of the waveguide. As illustrated, the optical mode has a substantial elliptical shape with the field intensity decreasing with the increase of distance to the center of the optical mode. The field intensity may have another shape depending on the configuration of the integrated device.

In FIG. 2-7A, a shape 2-118 is drawn to illustrate an example of the locations having an equal field intensity. The field may decay rapidly in a vertical direction that is parallel to the thickness of the waveguide. Also, as the waveguide traverses away from the excitation source, the power at the center of the waveguide decays in a horizontal direction that is parallel to the length of the waveguide and perpendicular to the width w and thickness t of the waveguide. Modulating the vertical extent of the optical mode of a waveguide along the length of the waveguide may bring sample wells that are farther away from the excitation source closer to the waveguide, and therefore enable as close to as possible the same amount of light to be delivered to the sample wells along the length of a waveguide and/or across different regions of an array.

In some embodiments, the vertical extent of the optical mode may be modulated by changing the thickness t of a waveguide along the length of the waveguide. For example, the thickness t of a waveguide may be increased as the waveguide extends away from the excitation source so as to bring the waveguide closer to sample wells that are farther away from the excitation source. In some embodiments, the thickness t of a waveguide may be modulated by transferring a topography of a photoresist layer to the waveguide core layer. The photoresist layer may be deposited on top of the waveguide core layer and provided with a desired surface profile after a grayscale lithography. Then the desired surface profile of the photoresist layer may be transferred to the waveguide core layer after a non-selective etch. It should be appreciated that the above is provided as an example and any other suitable fabrication processes may be used to provide a waveguided with a desired changing thickness along its length.

Additionally or alternatively, in some embodiments, the refractive index of the waveguides and/or the refractive index of its surrounding cladding material may be modulated. For example, ion implantation methods may be used to change the local composition of the waveguide core layer and/or cladding layer, which in turn modulates the refractive index.

The waveguides may be fabricated from a waveguide core material that is transparent (e.g., having a propagation loss that is less than 2 dB/m) at the wavelength of the excitation energy. For example, silicon nitride may be used as material for guiding excitation energy. Other materials that can be suitable for forming the waveguide core include silicon carbide and alloys of silicon nitride and silicon carbide. The waveguide cladding layer may be fabricated from a transparent material that provides a desired decay rate with respect to the waveguide core material. For example, silicon dioxide may be used as material for a cladding layer. These waveguide core and cladding materials may be deposited by methods such as plasma enhanced chemical vapor deposition (PECVD), and the optical properties of the materials may be tuned by adjusting the deposition parameters.

In some embodiments, the distances between a waveguide and respective sample wells may be modulated by modulating the lateral position of the sample wells with respect to the waveguide along the length of the waveguide. FIG. 2-8 illustrates such an example. As illustrated, the sample wells 2-102 may be disposed such that, along the length of a waveguide 2-104, sample wells that are closer in distance to the beginning end 2-108 of the waveguide array 2-100 are offset more from a center line of the waveguide than sample wells that are closer in distance to the array ending end 2-110 of the waveguide array 2-100. The offset may be in a direction perpendicular to the direction that the waveguide extends. As a result, the sample wells that are farther away from the excitation source are closer in distance to the waveguide than the sample wells that are closer in distance to the excitation source. It should be appreciated that the above is provided as an example and any suitable arrangement of the sample wells relative to the waveguides may be configured for modulating the distances between the waveguides and respective sample wells.

Figures 1, 2:
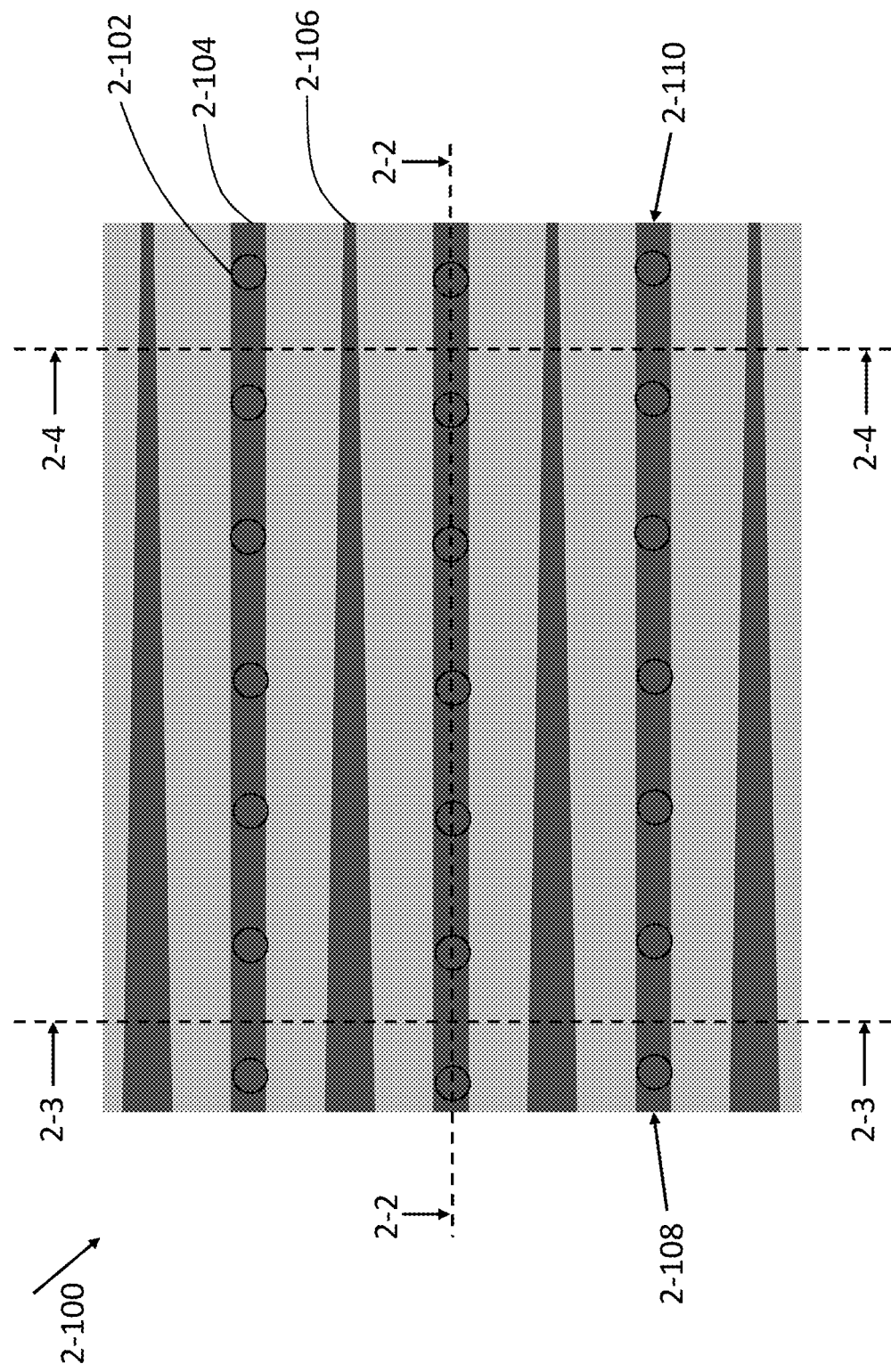
Figure 2:
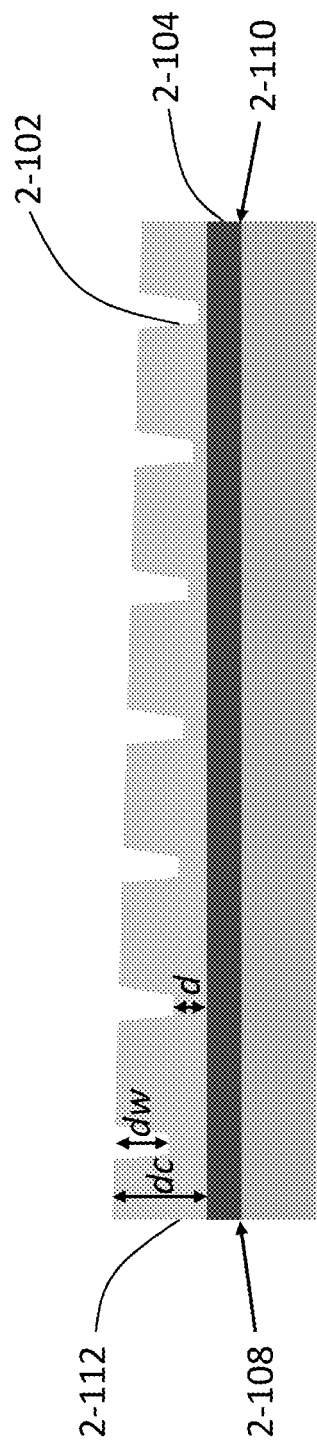
Figures 2, 3, 4, 5, 6, 7, 7A:
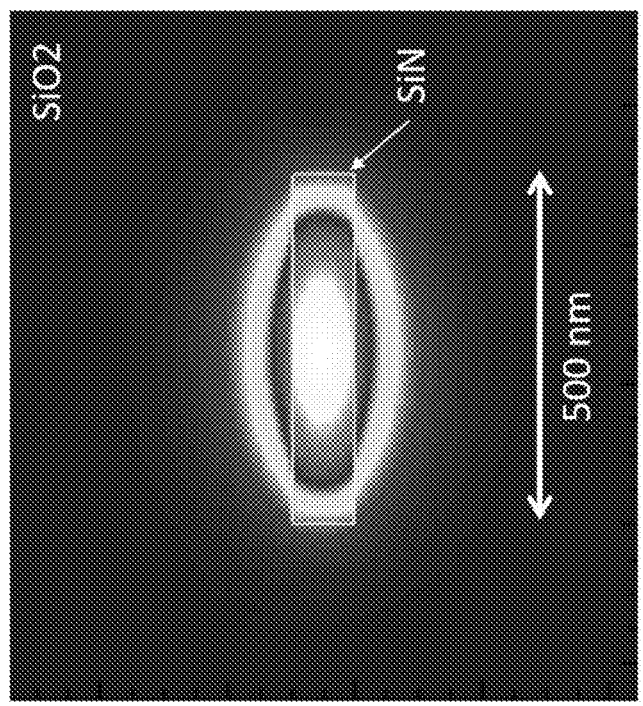
Figures 2, 3, 4, 5, 6, 7, 7B:
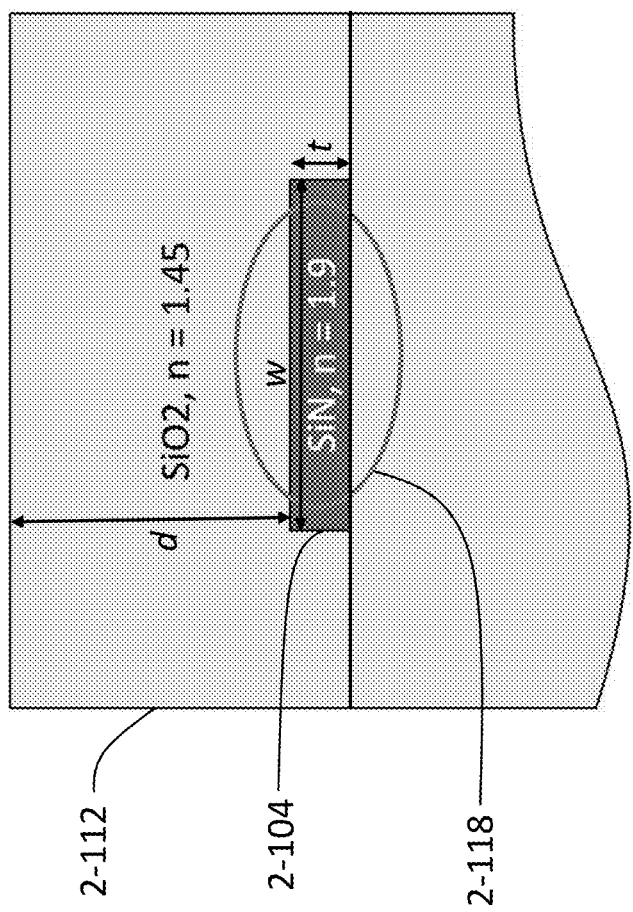
Figures 2, 3, 4, 5, 6, 7, 8:
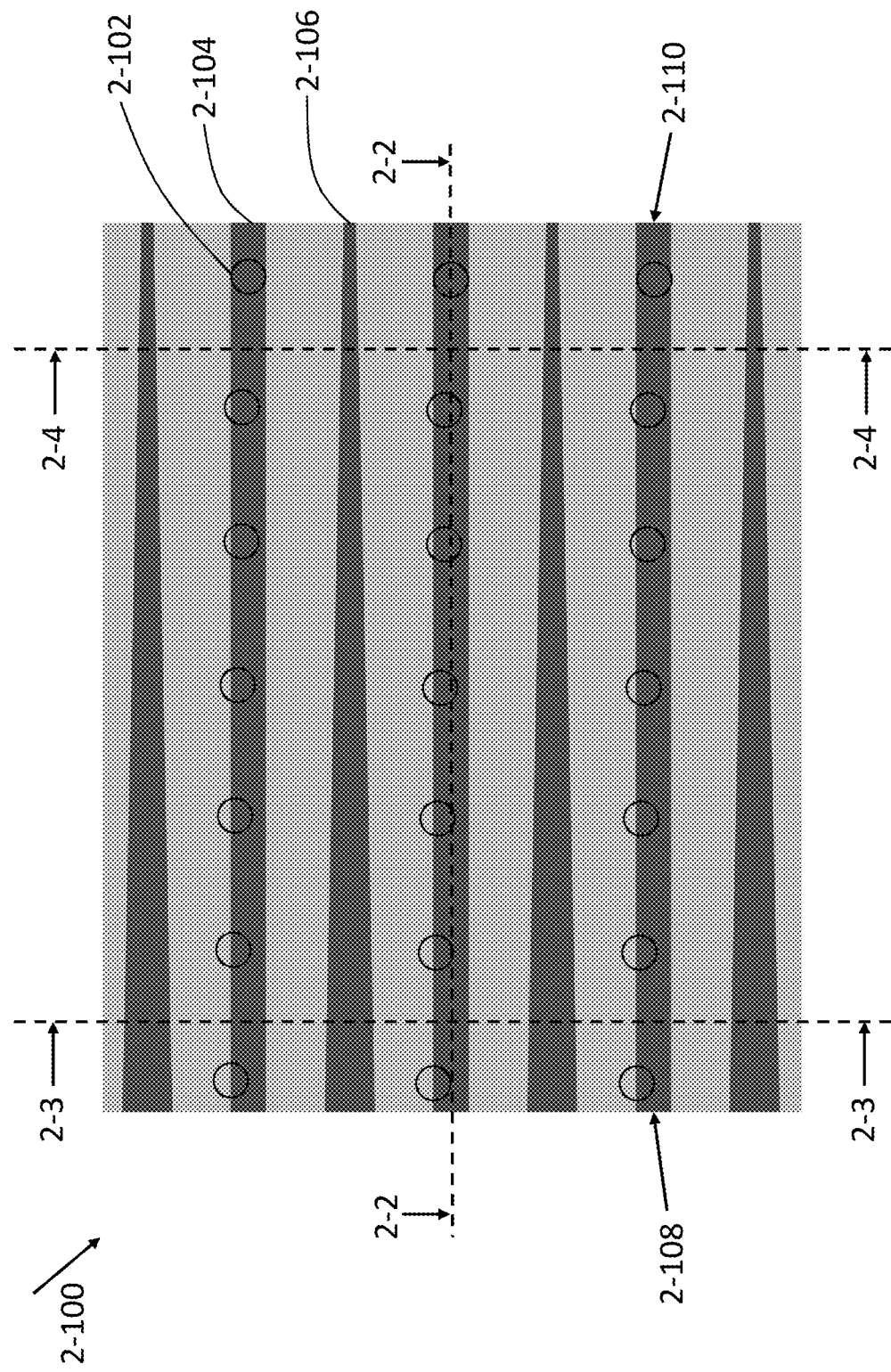
Figures 1, 3:
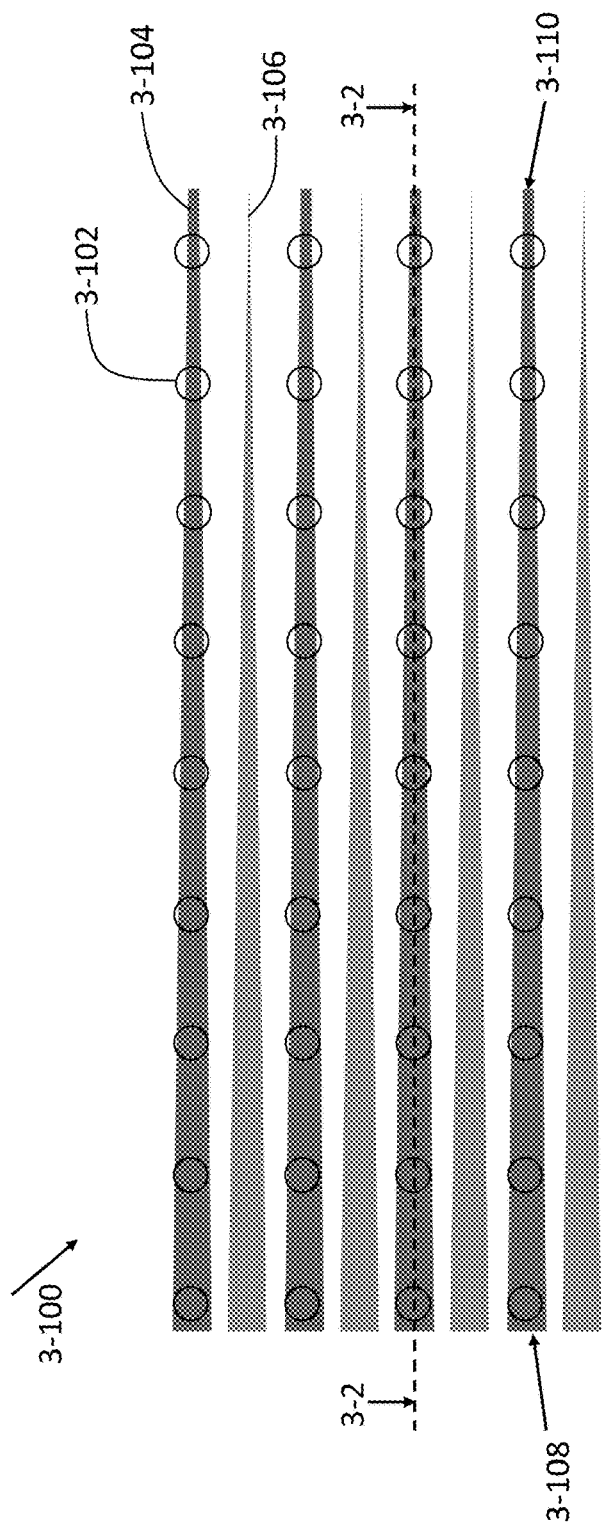

In some embodiments, the vertical extent of the optical mode of a waveguide may be modulated by waveguides with tapered widths along the length of the waveguides. FIG. 3-1 illustrates a planar schematic of a waveguide array 3-100, according to some embodiments. The waveguide array 3-100 may extend from an array beginning end 3-108 to an array ending end 3-110. The array beginning end 3-108 may be closer in distance to an excitation source than the array ending end 3-110. The waveguide array 3-100 may include waveguides 3-104 and dummy structures 3-106 disposed in between adjacent waveguides 3-104. Sample wells 3-102 may be disposed on top of the waveguides 3-104. There may be no sample wells disposed on top of the dummy structures 3-106.

The waveguide array 3-100 may have a modulated pattern density. In the illustrated example, the waveguides 3-104 have tapered widths along the length of the waveguides. The tapered waveguides may be configured to provide a weaker evanescent field closer to the excitation source and a stronger evanescent field distal for the excitation source. The tapered waveguides may also cause, from the array beginning end 3-108 to the array ending end 3-110, a decrease of the waveguide pattern density that can affect the result of a subsequent fabrication process. In the illustrated example, the dummy structures 3-106 also have tapered widths along the length of the dummy structures, which enhances the decrease of the waveguide pattern density from the array beginning end 3-108 to the array ending end 3-110.

As illustrated, the degrees of tapering, which may be measured by the slope of the outline of a waveguide 3-104 or a dummy structure 3-106 along their respective lengths, may be modulated to enable the substantially uniform distribution of excitation energy. In the illustrated example, the degree of tapering for a dummy structure 3-106 is steeper than the degree of tapering for a waveguide 3-104. It should be appreciated that a waveguide 3-104 may have a similar degree of tapering as or a steeper degree of tapering than a dummy structure 3-106.

The waveguide array 3-100 may be fabricated with a method similar to the first method illustrated in FIGS. 2-3A-2-4C, a method similar to the second method illustrated in FIGS. 2-5A-2-6B, or any suitable combination of the steps of the first and second methods. The resulting waveguide array 3-100 may have a tapered cladding layer similar to the cladding layer 2-112 illustrated in FIG. 2-2.

In some embodiments, waveguides and dummy structures may taper in opposite directions so as to provide a substantially constant pattern across an array of waveguides. FIG. 4-1 illustrates a planar schematic of a waveguide array 4-100, according to some embodiments. The waveguide array 4-100 may extend from an array beginning end 4-108 to an array ending end 4-110. The array beginning end 4-108 may be closer in distance to an excitation source than the array ending end 4-110. The waveguide array 4-100 may include waveguides 4-104 and dummy structures 4-106 disposed in between adjacent waveguides 4-104. Sample wells 4-102 may be disposed on top of the waveguides 4-104. There may be no sample wells disposed on top of the dummy structures 4-106.

Figures 1, 4:
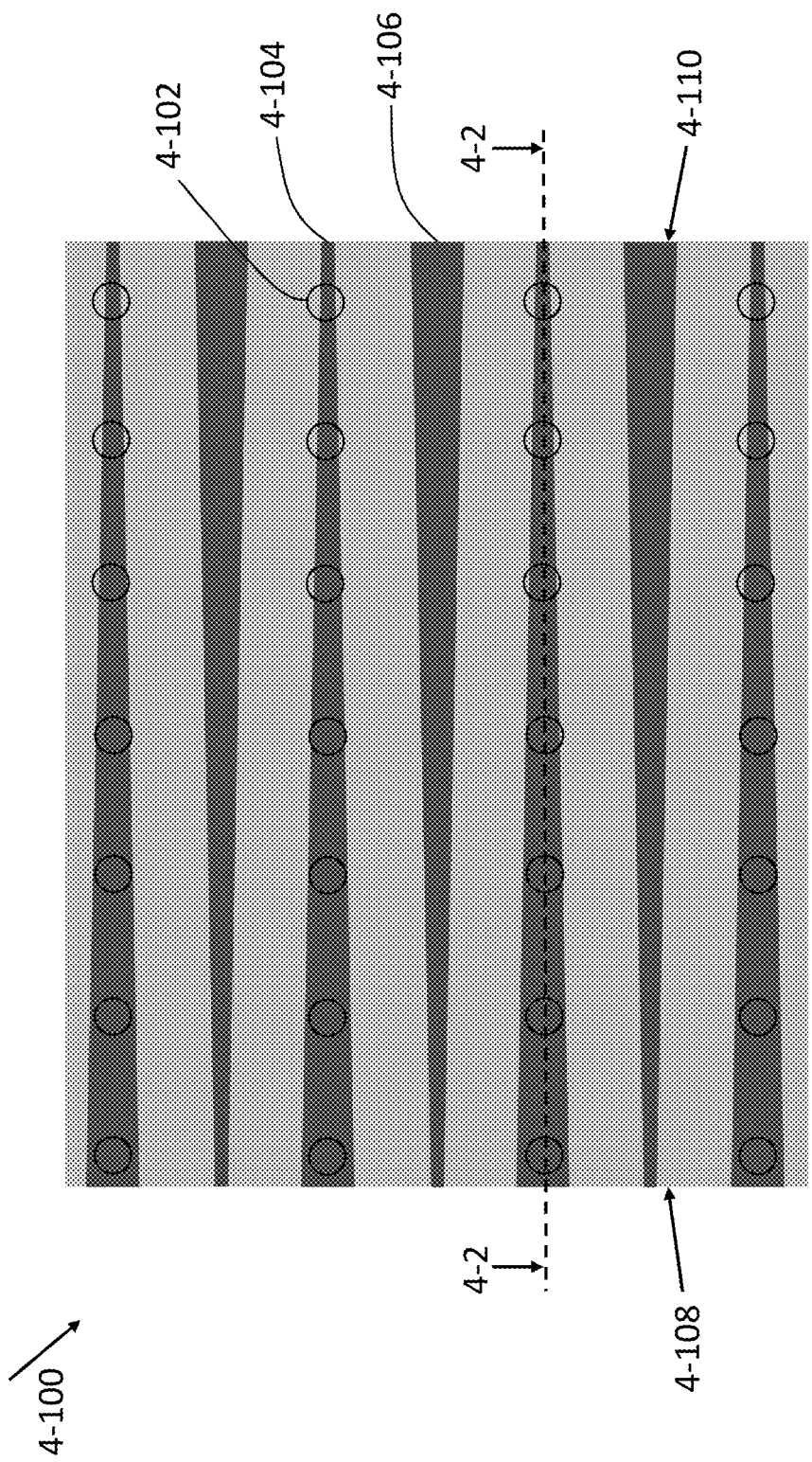
Figures 2B, 4:
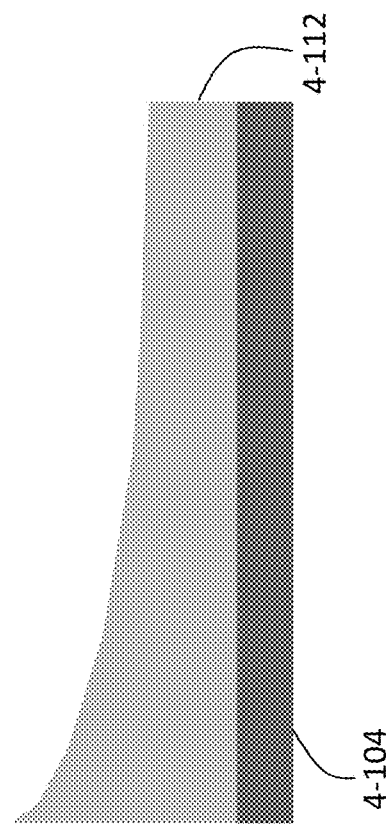
Figures 2A, 4:
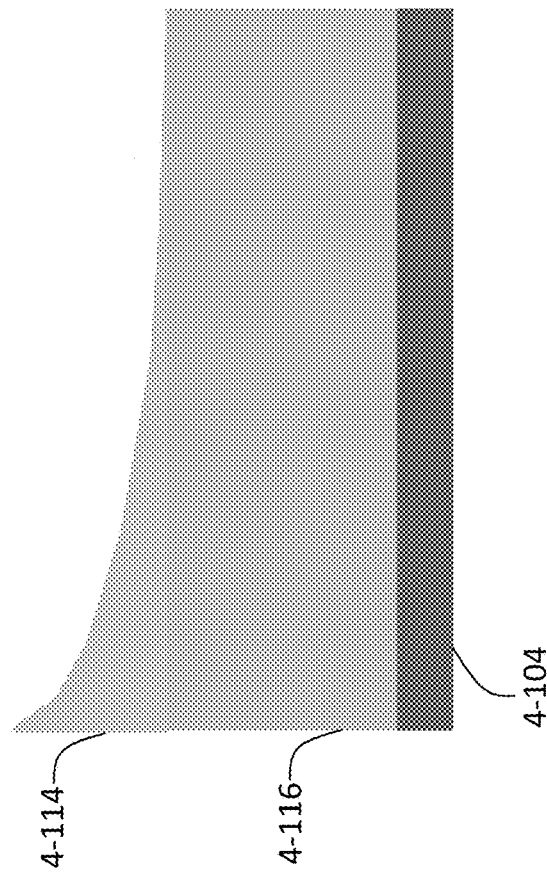

In some embodiments, the waveguide array 4-100 may be fabricated with a method illustrated in FIGS. 4-2A-4-2B. FIGS. 4-2A-4-2B are cross-sectional views of the waveguide array 4-100 along the line marked "4-2," according to some embodiments.

Before the fabrication steps illustrated in FIGS. 4-2A-4-2B, similar to the fabrication step illustrated in FIG. 2-3A and FIG. 2-4A, the waveguides 4-104 and dummy structures 4-106 may be fabricated by depositing a layer of waveguide core material on a substrate and patterning the layer of waveguide core material by lithography and etching. Similar to the fabrication step illustrated in FIG. 2-3B and FIG. 2-4B, a cladding layer may be deposited on top of the patterned layer of waveguide core material using a deposition process substantially independent of the underlying pattern density, for example, PECVD. Similar to the fabrication step illustrated in FIG. 2-3C and FIG. 2-4C, the cladding layer may be formed after polishing/planarizing the deposited cladding layer using, for example, a chemical mechanical polishing (CMP) process. As the waveguide array 4-100 has a substantially constant pattern across the array, the polished cladding layer may have a substantially flat surface.

In the fabrication step illustrated in FIG. 4-2A, a photoresist layer 4-144 may be deposited on top of the polished cladding layer 4-116 and provided with a tapered surface profile after a grayscale lithography. In the fabrication step illustrated in FIG. 4-2B, the tapered surface profile of the photoresist layer 4-114 may be transferred to the cladding layer 4-112 after a non-selective etch. The resulting waveguide array 4-100 may have a tapered cladding layer similar to the cladding layer 2-112 illustrated in FIG. 2-2.

Although steps of fabricating the waveguide arrays are described, it should be appreciated that the fabrication steps may be processed in any suitable combination and/or in any suitable sequence, and have any other suitable steps added therein.

C. Grating Coupler

As discussed in connection with FIG. 1-1, the integrated device may include a grating coupler, such as grating coupler 1-216, configured to receive light from an optical source and direct light to the waveguides configured to optically couple with the sample well array. The inventors have recognized and appreciated that some grating coupler configurations provide one or more benefits to the integrated device, including higher coupling efficiency of light to other optical components in the device and a broader tolerance for the angle of the incident light. A grating coupler includes multiple material structures, or grating teeth, separated by gaps filled a material. The material structures may have a higher refractive index than the gap material (e.g. material structures formed of silicon nitride and the gaps formed of silicon oxide). Parameters that may impact the coupling efficiency of a grating coupler include the width of the material structures, the number of material structures, the width of the gaps, the filling factor, which is the ratio of the width of the material structures to the width of the gaps.

Some embodiments relate to an integrated device having an apodized grating coupler configured to receive light incident to the integrated device. The apodized grating coupler may have material structures spaced from each other with a variable fill factor. In some embodiments, the material structures may be spaced apart from each other by gaps of variable widths. In some embodiments, the material structures may have variable widths.

Some embodiments relate to grating couplers having asymmetric material structures about a plane substantially parallel to a surface of the integrated device. In some embodiments, a grating coupler may have multiple layers. A blazed grating coupler includes a combination of grating couplers where the layer proximate to the surface has material structures with a smaller width than another layer. A blazed grating coupler may have saw teeth material structures, according to some embodiments. A bi-layer grating coupler includes a combination to two grating couplers offset from each other.

For some grating couplers, the coupling efficiency and range of incident angles for which a desired coupling efficiency can be achieved may depend on the bandwidth of the incident light where performance of a grating coupler may decrease for broader bands of wavelengths. The inventors have recognized and appreciated that a grating coupler may accommodate broader bands by altering the refractive index of the material structures, resulting in a wideband grating coupler. In some embodiments, multiple materials may be used to control the refractive index of the gratings. For example, if the silicon oxide and silicon nitride are used to form grating structures of a grating coupler, the grating structures may be discretized into sub-wavelength elements (e.g., less than 200 nm). The effective refractive index, $n_{eff}$, may depend on the filling factors for both silicon oxide, $f_{ox}$ and $f_{SiN}$, respectively, as well as the refractive index for silicon oxide, $n_{ox}$, and the refractive index for silicon nitride, $n_{SiN}$. In particular, $n_{eff} = \sqrt{f_{ox}n_{ox}^2 + f_{SiN}n_{SiN}^2}$.

It should be appreciated that a grating coupler having a configuration as described herein may couple with any suitable number of waveguides and may have output light in one or more directions. In some embodiments, a grating coupler may have multiple output waveguides substantially parallel in one direction III. Additional Aspects of the System The system may include an integrated device and an instrument configured to interface with the integrated device. The integrated device may include an array of pixels, where a pixel includes a sample well and at least one photodetector. A surface of the integrated device may have a plurality of sample wells, where a sample well is configured to receive a sample from a sample placed on the surface of the integrated device. A sample may contain multiple samples, and in some embodiments, different types of samples. The plurality of sample wells may have a suitable size and shape such that at least a portion of the sample wells receive one sample from a sample. In some embodiments, the number of samples within a sample well may be distributed among the sample wells such that some sample wells contain one sample with others contain zero, two or more samples.

In some embodiments, a sample may contain multiple single-stranded DNA templates, and individual sample wells on a surface of an integrated device may be sized and shaped to receive a sequencing template. Sequencing templates may be distributed among the sample wells of the integrated device such that at least a portion of the sample wells of the integrated device contain a sequencing template. The sample may also contain labeled nucleotides which then enter in the sample well and may allow for identification of a nucleotide as it is incorporated into a strand of DNA complementary to the single-stranded DNA template in the sample well. In such an example, the "sample" may refer to both the sequencing template and the labeled nucleotides currently being incorporated by a polymerase. In some embodiments, the sample may contain sequencing templates and labeled nucleotides may be subsequently introduced to a sample well as nucleotides are incorporated into a complementary strand within the sample well. In this manner, timing of incorporation of nucleotides may be controlled by when labeled nucleotides are introduced to the sample wells of an integrated device.

Excitation light is provided from an excitation source located separate from the pixel array of the integrated device. The excitation light is directed at least in part by elements of the integrated device towards one or more pixels to illuminate an illumination region within the sample well. A marker may then emit emission light when located within the illumination region and in response to being illuminated by excitation light. In some embodiments, one or more excitation sources are part of the instrument of the system where components of the instrument and the integrated device are configured to direct the excitation light towards one or more pixels.

Emission light emitted by a sample may then be detected by one or more photodetectors within a pixel of the integrated device. Characteristics of the detected emission light may provide an indication for identifying the marker associated with the emission light. Such characteristics may include any suitable type of characteristic, including an arrival time of photons detected by a photodetector, an amount of photons accumulated over time by a photodetector, and/or a distribution of photons across two or more photodetectors. In some embodiments, a photodetector may have a configuration that allows for the detection of one or more timing characteristics associated with a sample's emission light (e.g., fluorescence lifetime). The photodetector may detect a distribution of photon arrival times after a pulse of excitation light propagates through the integrated device, and the distribution of arrival times may provide an indication of a timing characteristic of the sample's emission light (e.g., a proxy for fluorescence lifetime). In some embodiments, the one or more photodetectors provide an indication of the probability of emission light emitted by the marker (e.g., fluorescence intensity). In some embodiments, a plurality of photodetectors may be sized and arranged to capture a spatial distribution of the emission light. Output signals from the one or more photodetectors may then be used to distinguish a marker from among a plurality of markers, where the plurality of markers may be used to identify a sample within the sample. In some embodiments, a sample may be excited by multiple excitation energies, and emission light and/or timing characteristics of the emission light emitted by the sample in response to the multiple excitation energies may distinguish a marker from a plurality of markers.

Figures 1A, 5:
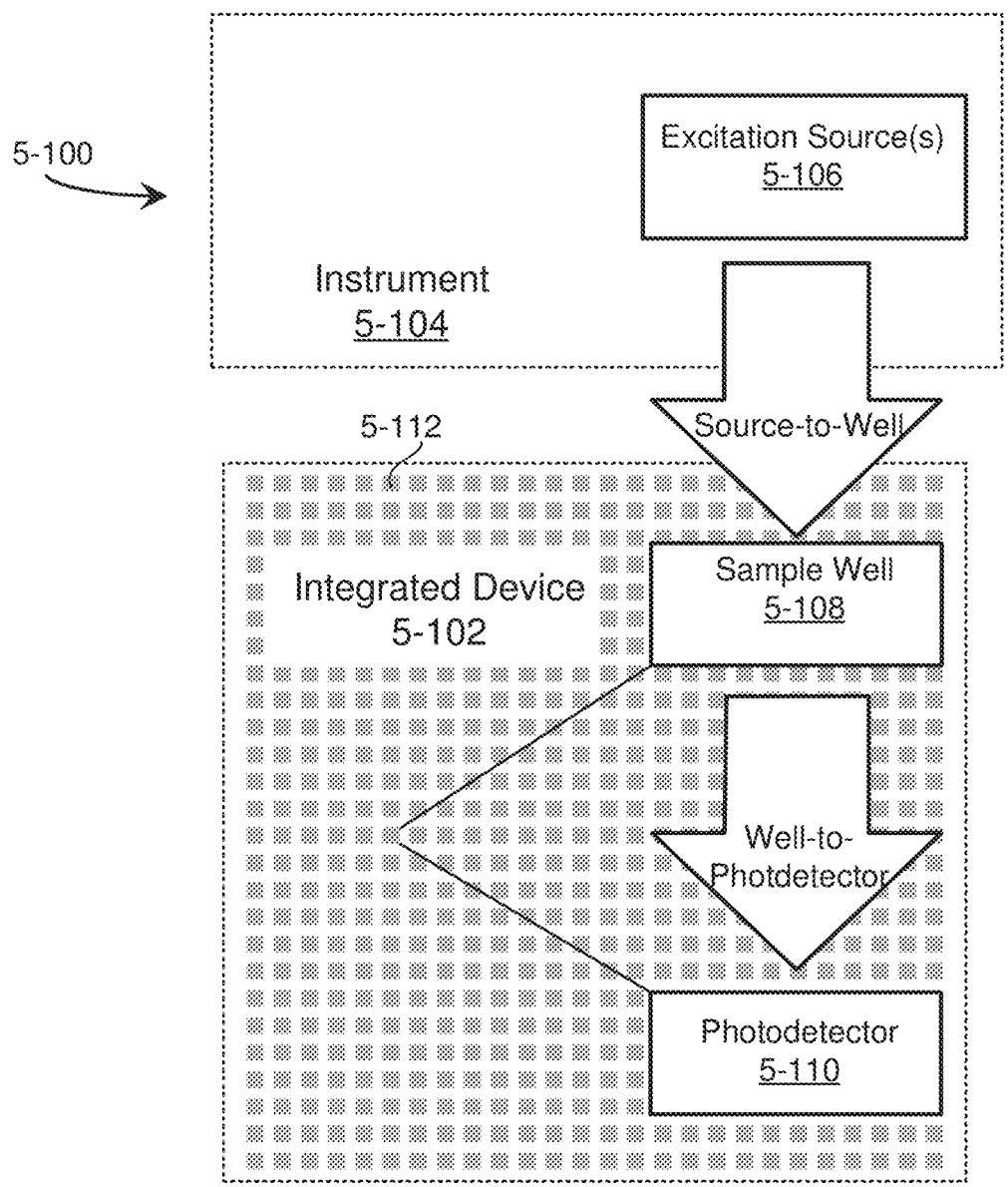

A schematic overview of the system 5-100 is illustrated in FIG. 5-1A. The system comprises both an integrated device 5-102 that interfaces with an instrument 5-104. In some embodiments, instrument 5-104 may include one or more excitation sources 5-106 integrated as part of instrument 5-104. In some embodiments, an excitation source may be external to both instrument 5-104 and integrated device 5-102, and instrument 5-104 may be configured to receive excitation light from the excitation source and direct excitation light to the integrated device. The integrated device may interface with the instrument using any suitable socket for receiving the integrated device and holding it in precise optical alignment with the excitation source. The excitation source 5-106 may be configured to provide excitation light to the integrated device 5-102. As illustrated schematically in FIG. 5-1A, the integrated device 5-102 has a plurality of pixels 5-112, where at least a portion of pixels may perform independent analysis of a sample. Such pixels 5-112 may be referred to as "passive source pixels" since a pixel receives excitation light from a source 5-106 separate from the pixel, where excitation light from the source excites some or all of the pixels 5-112. Excitation source 5-106 may be any suitable light source. Examples of suitable excitation sources are described in U.S. patent application Ser. No. 14/821,688, filed Aug. 7, 2015, titled "INTEGRATED DEVICE FOR PROBING, DETECTING AND ANALYZING MOLECULES," which is incorporated by reference in its entirety. In some embodiments, excitation source 5-106 includes multiple excitation sources that are combined to deliver excitation light to integrated device 5-102. The multiple excitation sources may be configured to produce multiple excitation energies or wavelengths.

A pixel 5-112 has a sample well 5-108 configured to receive a sample and a photodetector 5-110 for detecting emission light emitted by the sample in response to illuminating the sample with excitation light provided by the excitation source 5-106. In some embodiments, sample well 5-108 may retain the sample in proximity to a surface of integrated device 5-102, which may case delivery of excitation light to the sample and detection of emission light from the sample.

Optical elements for coupling excitation light from excitation light source 5-106 to integrated device 5-102 and guiding excitation light to the sample well 5-108 are located both on integrated device 5-102 and the instrument 5-104. Source-to-well optical elements may comprise one or more grating couplers located on integrated device 5-102 to couple excitation light to the integrated device and waveguides to deliver excitation light from instrument 5-104 to sample wells in pixels 5-112. One or more optical splitter elements may be positioned between a grating coupler and the waveguides. The optical splitter may couple excitation light from the grating coupler and deliver excitation light to at least one of the waveguides. In some embodiments, the optical splitter may have a configuration that allows for delivery of excitation light to be substantially uniform across all the waveguides such that each of the waveguides receives a substantially similar amount of excitation light. Such embodiments may improve performance of the integrated device by improving the uniformity of excitation light received by sample wells of the integrated device.

Sample well 5-108, a portion of the excitation source-to-well optics, and the sample well-to-photodetector optics are located on integrated device 5-102. Excitation source 5-106 and a portion of the source-to-well components are located in instrument 5-104. In some embodiments, a single component may play a role in both coupling excitation light to sample well 5-108 and delivering emission light from sample well 5-108 to photodetector 5-110. Examples of suitable components, for coupling excitation light to a sample well and/or directing emission light to a photodetector, to include in an integrated device are described in U.S. patent application Ser. No. 14/821,688, filed Aug. 7, 2015, titled "INTEGRATED DEVICE FOR PROBING, DETECTING AND ANALYZING MOLECULES," and U.S. patent application Ser. No. 14/543,865, filed Nov. 17, 2014, titled "INTEGRATED DEVICE WITH EXTERNAL LIGHT SOURCE FOR PROBING, DETECTING, AND ANALYZING MOLECULES," each of which is incorporated herein by reference in its entirety.

Pixel 5-112 is associated with its own individual sample well 5-108 and at least one photodetector 5-110. The plurality of pixels of integrated device 5-102 may be arranged to have any suitable shape, size, and/or dimensions. Integrated device 5-102 may have any suitable number of pixels. The number of pixels in integrated device 2-102 may be in the range of approximately 10,000 pixels to 1,000,000 pixels or any value or range of values within that range. In some embodiments, the pixels may be arranged in an array of 512 pixels by 512 pixels. Integrated device 5-102 may interface with instrument 5-104 in any suitable manner. In some embodiments, instrument 5-104 may have an interface that detachably couples to integrated device 5-102 such that a user may attach integrated device 5-102 to instrument 5-104 for use of integrated device 5-102 to analyze a sample and remove integrated device 5-102 from instrument 5-104 to allow for another integrated device to be attached. The interface of instrument 5-104 may position integrated device 5-102 to couple with circuitry of instrument 5-104 to allow for readout signals from one or more photodetectors to be transmitted to instrument 5-104. Integrated device 5-102 and instrument 5-104 may include multi-channel, high-speed communication links for handling data associated with large pixel arrays (e.g., more than 10,000 pixels).

Figures 1B, 5:
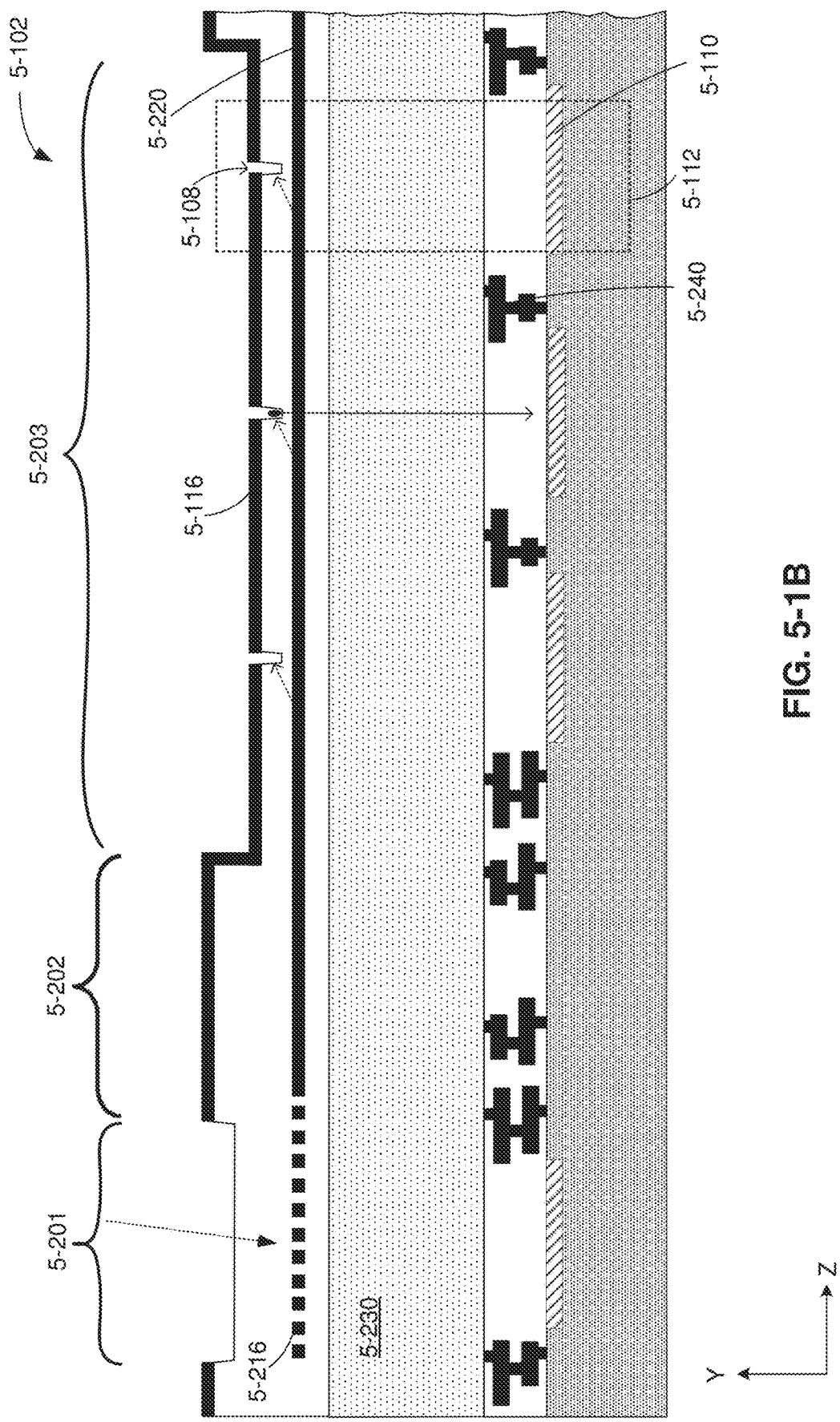
Figures 2, 5:
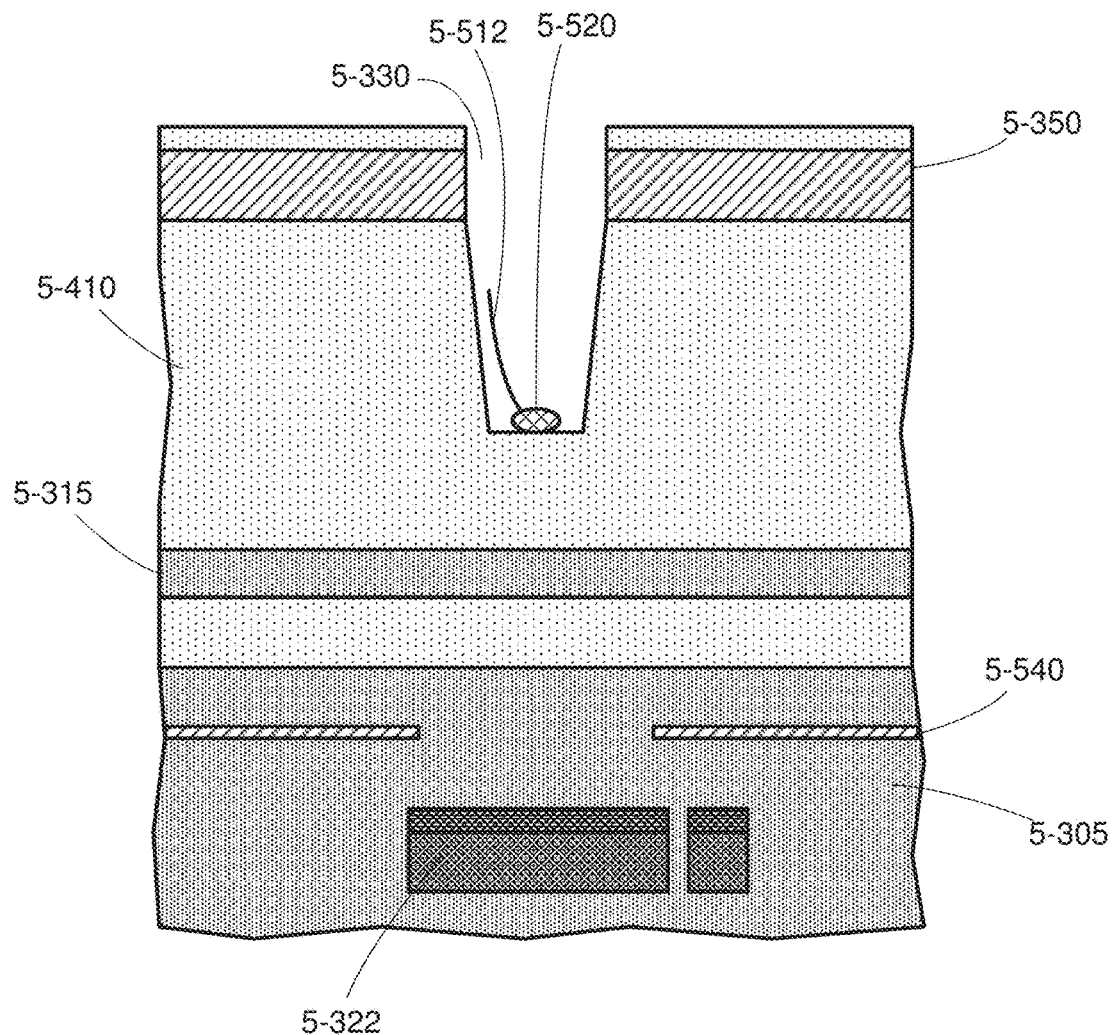
Figures 3, 5:
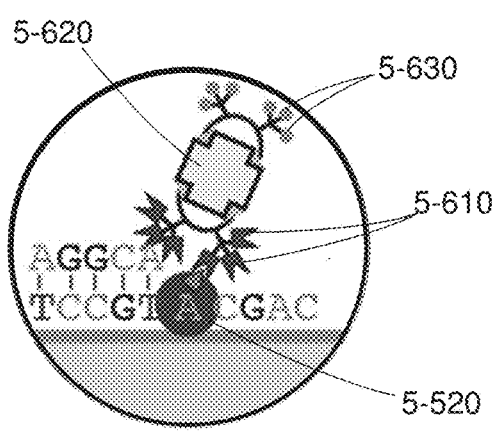
Figures 4, 5:
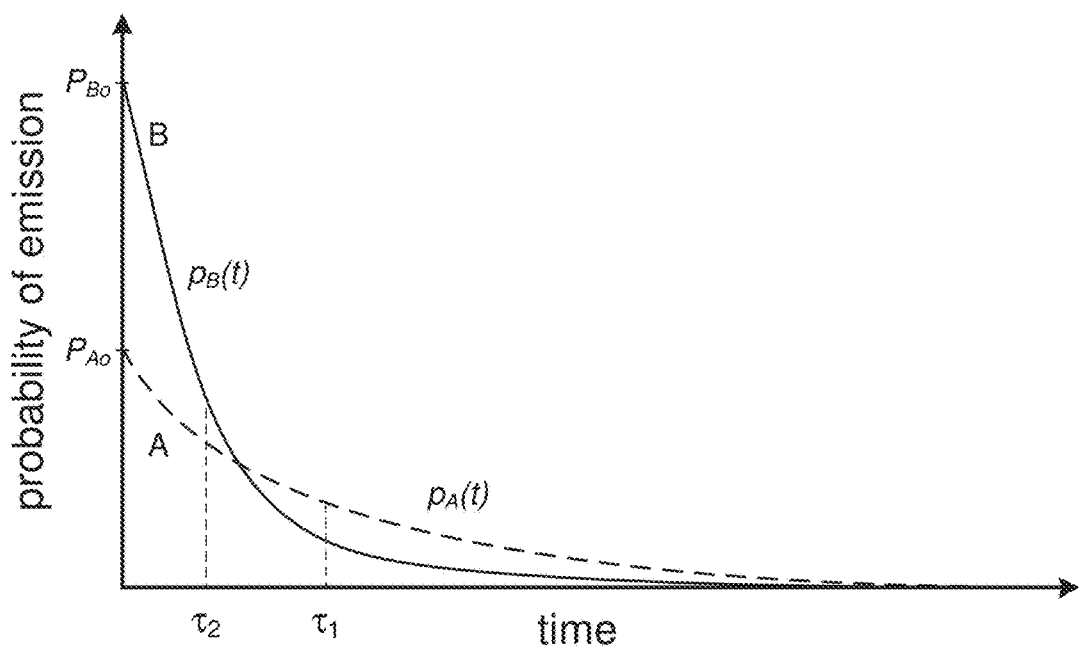
Figure 5:
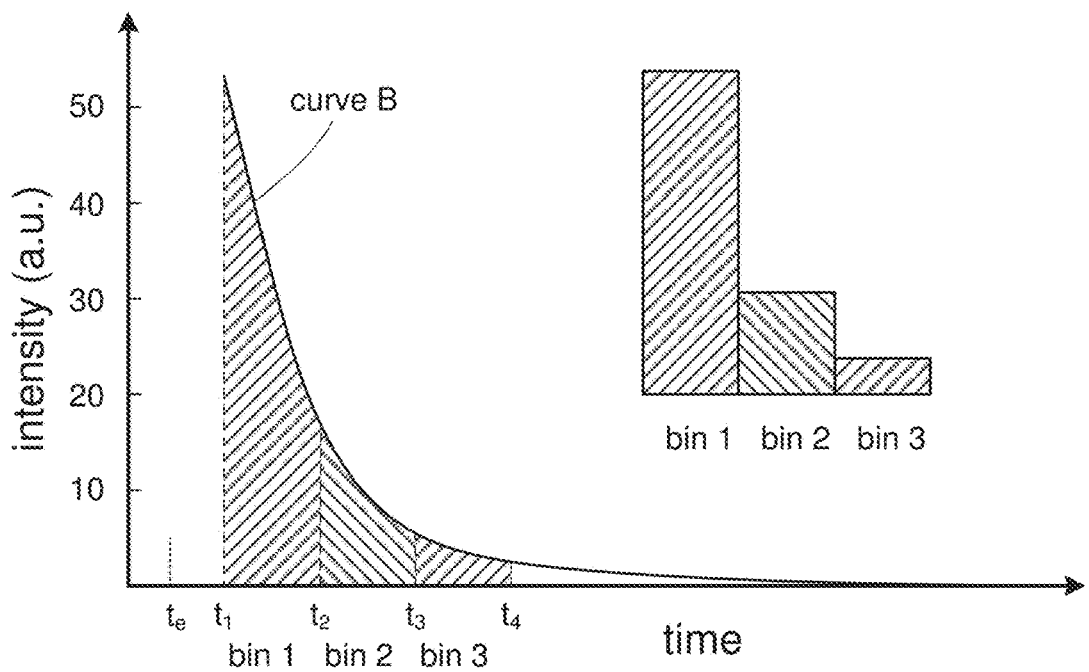
Figures 5, 6:
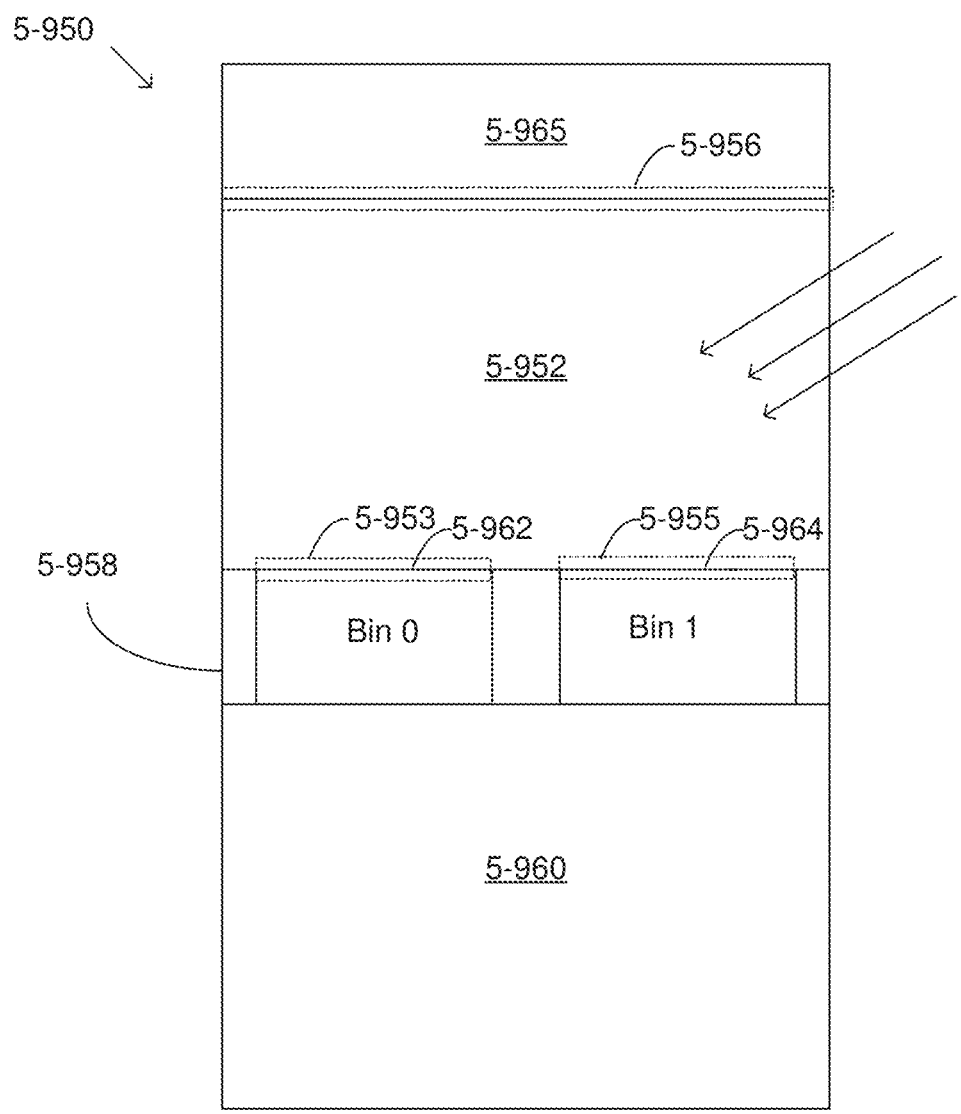
Figures 5, 6, 7, 7A:
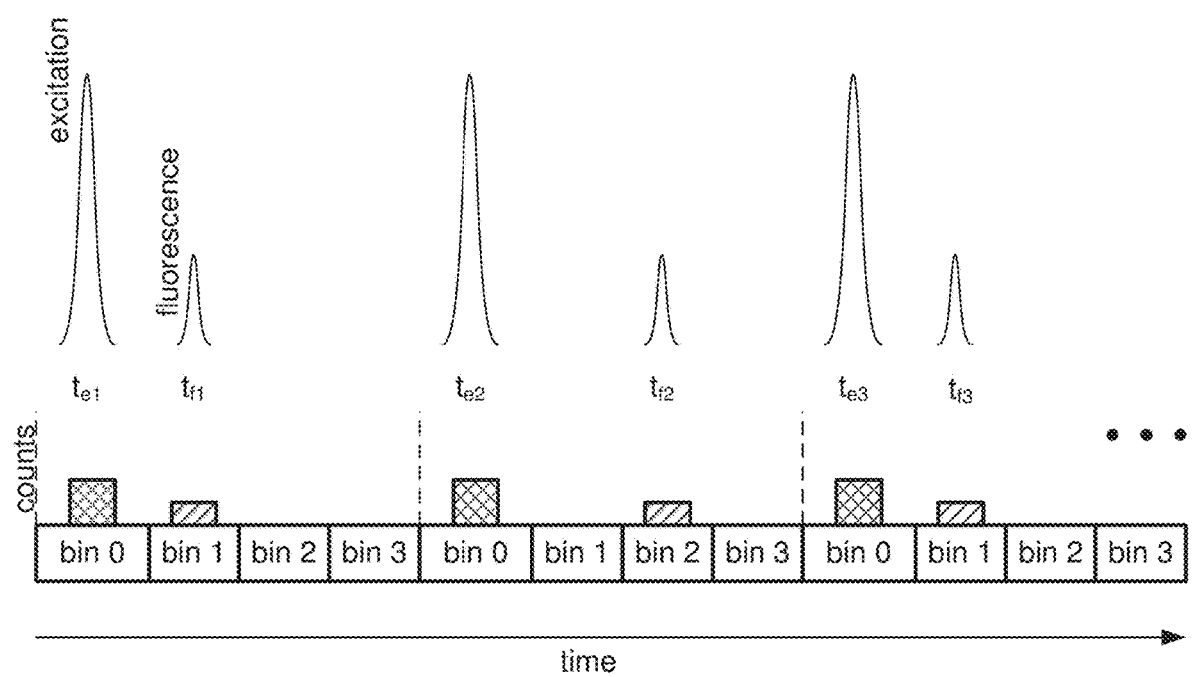
Figures 5, 6, 7, 7B:
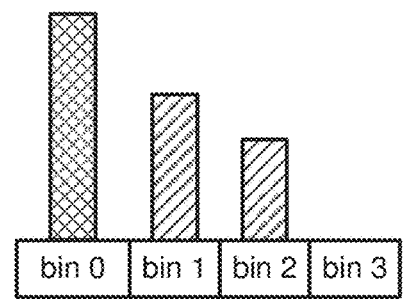
Figures 5, 6, 7, 8, 8A:
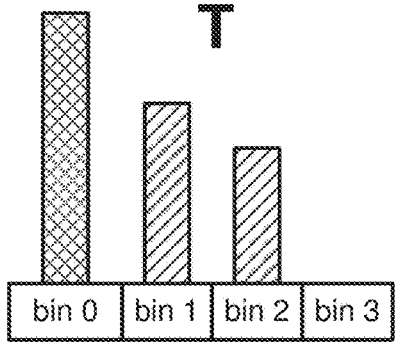
Figures 5, 6, 7, 8, 8B:
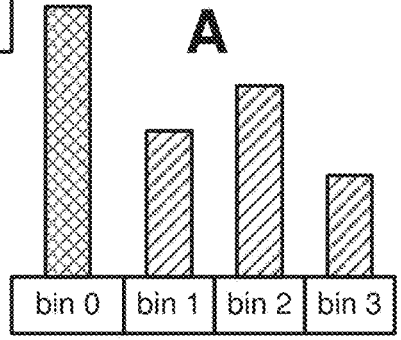
Figures 5, 6, 7, 8, 8C:
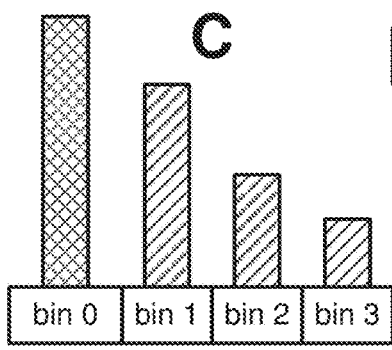
Figures 5, 6, 7, 8, 8D:
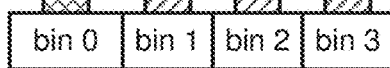

A cross-sectional schematic of integrated device 5-102 illustrating a row of pixels 5-112 is shown in FIG. 5-1B. Integrated device 5-102 may include coupling region 5-201, routing region 5-202, and pixel region 5-203. Pixel region 5-203 may include a plurality of pixels 5-112 having sample wells 5-108 positioned on a surface at a location separate from coupling region 5-201, which is where excitation light (shown as the dashed arrow) couples to integrated device 5-102. Sample wells 5-108 may be formed through metal layer(s) 5-116. One pixel 5-112, illustrated by the dotted rectangle, is a region of integrated device 5-102 that includes a sample well 5-108 and photodetector region having one or more photodetectors 5-110.

FIG. 5-1B illustrates the path of excitation (shown in dashed lines) by coupling a beam of excitation light to coupling region 5-201 and to sample wells 5-108. The row of sample wells 5-108 shown in FIG. 5-1B may be positioned to optically couple with waveguide 5-220. Excitation light may illuminate a sample located within a sample well. The sample may reach an excited state in response to being illuminated by the excitation light. When a sample is in an excited state, the sample may emit emission light, which may be detected by one or more photodetectors associated with the sample well. FIG. 5-1B schematically illustrates the path of emission light (shown as the solid line) from a sample well 5-108 to photodetector(s) 5-110 of pixel 5-112. The photodetector(s) 5-110 of pixel 5-112 may be configured and positioned to detect emission light from sample well 5-108. Examples of suitable photodetectors are described in U.S. patent application Ser. No. 14/821,656, filed Aug. 7, 2015, titled "INTEGRATED DEVICE FOR TEMPORAL BINNING OF RECEIVED PHOTONS," which is incorporated by reference in its entirety. Additional examples of suitable photodetectors are described in U.S. patent application Ser. No. 15/852,571, filed Dec. 22, 2017, titled "INTEGRATED PHOTODETECTOR WITH DIRECT BINNING PIXEL," which is incorporated herein by reference in its entirety. For an individual pixel 5-112, a sample well 5-108 and its respective photodetector(s) 5-110 may be aligned along a common axis (along the y-direction shown in FIG. 5-1B). In this manner, the photodetector(s) may overlap with the sample well within a pixel 5-112.

The directionality of the emission light from a sample well 5-108 may depend on the positioning of the sample in the sample well 5-108 relative to metal layer(s) 5-116 because metal layer(s) 5-116 may act to reflect emission light. In this manner, a distance between metal layer(s) 5-116 and a fluorescent marker positioned in a sample well 5-108 may impact the efficiency of photodetector(s) 5-110, that are in the same pixel as the sample well, to detect the light emitted by the fluorescent marker. The distance between metal layer(s) 5-116 and the bottom surface of a sample well 5-106, which is proximate to where a sample may be positioned during operation, may be in the range of 100 nm to 500 nm, or any value or range of values in that range. In some embodiments the distance between metal layer(s) 5-116 and the bottom surface of a sample well 5-108 is approximately 300 nm.

The distance between the sample and the photodetector(s) may also impact efficiency in detecting emission light. By decreasing the distance light has to travel between the sample and the photodetector(s), detection efficiency of emission light may be improved. In addition, smaller distances between the sample and the photodetector(s) may allow for pixels that occupy a smaller area footprint of the integrated device, which can allow for a higher number of pixels to be included in the integrated device. The distance between the bottom surface of a sample well 5-108 and photodetector(s) may be in the range of 1 μm to 15 μm, or any value or range of values in that range.

Photonic structure(s) 5-230 may be positioned between sample wells 5-108 and photodetectors 5-110 and configured to reduce or prevent excitation light from reaching photodetectors 5-110, which may otherwise contribute to signal noise in detecting emission light. As shown in FIG. 5-1B, the one or more photonic structures 5-230 may be positioned between waveguide 5-220 and photodetectors 5-110. Photonic structure(s) 5-230 may include one or more optical rejection photonic structures including a spectral filter, a polarization filter, and a spatial filter. Photonic structure(s) 5-230 may be positioned to align with individual sample wells 5-108 and their respective photodetector(s) 5-110 along a common axis. Metal layers 5-240, which may act as a circuitry for integrated device 5-102, may also act as a spatial filter, in accordance with some embodiments. In such embodiments, one or more metal layers 5-240 may be positioned to block some or all excitation light from reaching photodetector(s) 5-110.

Coupling region 5-201 may include one or more optical components configured to couple excitation light from an external excitation source. Coupling region 5-201 may include grating coupler 5-216 positioned to receive some or all of a beam of excitation light. Examples of suitable grating couplers are described in U.S. patent application Ser. No. 15/844,403, filed Dec. 15, 2017, titled "OPTICAL COUPLER AND WAVEGUIDE SYSTEM," which is incorporated by reference in its entirety. Grating coupler 5-216 may couple excitation light to waveguide 5-220, which may be configured to propagate excitation light to the proximity of one or more sample wells 5-108. Alternatively, coupling region 5-201 may comprise other well-known structures for coupling light into a waveguide.

Components located off of the integrated device may be used to position and align the excitation source 5-106 to the integrated device. Such components may include optical components including lenses, mirrors, prisms, windows, apertures, attenuators, and/or optical fibers. Additional mechanical components may be included in the instrument to allow for control of one or more alignment components. Such mechanical components may include actuators, stepper motors, and/or knobs. Examples of suitable excitation sources and alignment mechanisms are described in U.S. patent application Ser. No. 15/161,088, filed May 20, 2016, titled "PULSED LASER AND SYSTEM," which is incorporated by reference in its entirety. Another example of a beam-steering module is described in U.S. patent application Ser. No. 15/842,720, filed Dec. 14, 2017, titled "COMPACT BEAM SHAPING AND STEERING ASSEMBLY," which is incorporated herein by reference.

A sample to be analyzed may be introduced into sample well 5-108 of pixel 5-112. The sample may be a biological sample or any other suitable sample, such as a chemical sample. The sample may include multiple molecules and the sample well may be configured to isolate a single molecule. In some instances, the dimensions of the sample well may act to confine a single molecule within the sample well, allowing measurements to be performed on the single molecule. Excitation light may be delivered into the sample well 5-108, so as to excite the sample or at least one fluorescent marker attached to the sample or otherwise associated with the sample while it is within an illumination area within the sample well 5-108.

In operation, parallel analyses of samples within the sample wells are carried out by exciting some or all of the samples within the wells using excitation light and detecting signals from sample emission with the photodetectors. Emission light from a sample may be detected by a corresponding photodetector and converted to at least one electrical signal. The electrical signals may be transmitted along conducting lines (e.g., metal layers 5-240) in the circuitry of the integrated device, which may be connected to an instrument interfaced with the integrated device. The electrical signals may be subsequently processed and/or analyzed. Processing or analyzing of electrical signals may occur on a suitable computing device either located on or off the instrument.

Instrument 5-104 may include a user interface for controlling operation of instrument 5-104 and/or integrated device 5-102. The user interface may be configured to allow a user to input information into the instrument, such as commands and/or settings used to control the functioning of the instrument. In some embodiments, the user interface may include buttons, switches, dials, and a microphone for voice commands. The user interface may allow a user to receive feedback on the performance of the instrument and/or integrated device, such as proper alignment and/or information obtained by readout signals from the photodetectors on the integrated device. In some embodiments, the user interface may provide feedback using a speaker to provide audible feedback. In some embodiments, the user interface may include indicator lights and/or a display screen for providing visual feedback to a user.

In some embodiments, instrument 5-104 may include a computer interface configured to connect with a computing device. Computer interface may be a USB interface, a Fire Wire interface, or any other suitable computer interface. Computing device may be any general purpose computer, such as a laptop or desktop computer. In some embodiments, computing device may be a server (e.g., cloud-based server) accessible over a wireless network via a suitable computer interface. The computer interface may facilitate communication of information between instrument 5-104 and the computing device. Input information for controlling and/or configuring the instrument 5-104 may be provided to the computing device and transmitted to instrument 5-104 via the computer interface. Output information generated by instrument 5-104 may be received by the computing device via the computer interface. Output information may include feedback about performance of instrument 5-104, performance of integrated device 5-112, and/or data generated from the readout signals of photodetector 5-110.

In some embodiments, instrument 5-104 may include a processing device configured to analyze data received from one or more photodetectors of integrated device 5-102 and/or transmit control signals to excitation source(s) 2-106. In some embodiments, the processing device may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from one or more photodetectors may be performed by both a processing device of instrument 5-104 and an external computing device. In other embodiments, an external computing device may be omitted and processing of data from one or more photodetectors may be performed solely by a processing device of integrated device 5-102.

A non-limiting example of a biological reaction taking place in a sample well 5-330 is depicted in FIG. 5-2. In this example, sequential incorporation of nucleotides and/or nucleotide analogs into a growing strand that is complementary to a target nucleic acid is taking place in the sample well. The sequential incorporation can be detected to sequence a series of nucleic acids (e.g., DNA, RNA). The sample well may have a depth in the range of approximately 100 to approximately 500 nm, or any value or range of values within that range, and a diameter in the range of approximately 80 nm to approximately 200 nm. A metallization layer 5-540 (e.g., a metallization for an electrical reference potential) may be patterned above the photodetector to provide an aperture that blocks stray light from adjacent sample wells and other unwanted light sources. According to some embodiments, polymerase 5-520 may be located within the sample well 5-330 (e.g., attached to a base of the sample well). The polymerase may take up a target nucleic acid 5-510 (e.g., a portion of nucleic acid derived from DNA), and sequence a growing strand of complementary nucleic acid to produce a growing strand of DNA 5-512. Nucleotides and/or nucleotide analogs labeled with different fluorophores may be dispersed in a solution above and within the sample well.

When a labeled nucleotide and/or nucleotide analog 5-610 is incorporated into a growing strand of complementary nucleic acid, as depicted in FIG. 5-3, one or more attached fluorophores 5-630 may be repeatedly excited by pulses of optical energy coupled into the sample well 5-330 from the waveguide 5-315. In some embodiments, the fluorophore or fluorophores 5-630 may be attached to one or more nucleotides and/or nucleotide analogs 5-610 with any suitable linker 5-620. An incorporation event may last for a period of time up to about 100 ms. During this time, pulses of fluorescent emission resulting from excitation of the fluorophore(s) by pulses from the mode-locked laser may be detected with a time-binning photodetector 5-322. By attaching fluorophores with different emission characteristics (e.g., fluorescent decay rates, intensity, fluorescent wavelength) to the different nucleotides (A,C,G,T), detecting and distinguishing the different emission characteristics while the strand of DNA 5-512 incorporates a nucleic acid and enables determination of the nucleotide sequence of the growing strand of DNA.

According to some embodiments, an instrument 5-104 that is configured to analyze samples based on fluorescent emission characteristics may detect differences in fluorescent lifetimes and/or intensities between different fluorescent molecules, and/or differences between lifetimes and/or intensities of the same fluorescent molecules in different environments. By way of explanation, FIG. 5-4 plots two different fluorescent emission probability curves (A and B), which may be representative of fluorescent emission from two different fluorescent molecules, for example. With reference to curve A (dashed line), after being excited by a short or ultrashort optical pulse, a probability $p_A(t)$ of a fluorescent emission from a first molecule may decay with time, as depicted. In some cases, the decrease in the probability of a photon being emitted over time may be represented by an exponential decay function $p_A(t)=P_{Ao}e^{-t/\tau_A}$, where $P_{Ao}$ is an initial emission probability and $\tau_A$ is a temporal parameter associated with the first fluorescent molecule that characterizes the emission decay probability. $\tau_A$ may be referred to as the "fluorescence lifetime," "emission lifetime," or "lifetime" of the first fluorescent molecule. In some cases, the value of $\tau_A$ may be altered by a local environment of the fluorescent molecule. Other fluorescent molecules may have different emission characteristics than that shown in curve A. For example, another fluorescent molecule may have a decay profile that differs from a single exponential decay, and its lifetime may be characterized by a half-life value or some other metric.

A second fluorescent molecule may have a decay profile that is exponential, but has a measurably different lifetime $\tau_B$, as depicted for curve B in FIG. 5-4. In the example shown, the lifetime for the second fluorescent molecule of curve B is shorter than the lifetime for curve A, and the probability of emission is higher sooner after excitation of the second molecule than for curve A. Different fluorescent molecules may have lifetimes or half-life values ranging from about 0.1 ns to about 20 ns, in some embodiments.

The inventors have recognized and appreciated that differences in fluorescent emission lifetimes can be used to discern between the presence or absence of different fluorescent molecules and/or to discern between different environments or conditions to which a fluorescent molecule is subjected. In some cases, discerning fluorescent molecules based on lifetime (rather than emission wavelength, for example) can simplify aspects of an instrument 5-104. As an example, wavelength-discriminating optics (such as wavelength filters, dedicated detectors for each wavelength, dedicated pulsed optical sources at different wavelengths, and/or diffractive optics) may be reduced in number or eliminated when discerning fluorescent molecules based on lifetime. In some cases, a single pulsed optical source operating at a single characteristic wavelength may be used to excite different fluorescent molecules that emit within a same wavelength region of the optical spectrum but have measurably different lifetimes. An analytic system that uses a single pulsed optical source, rather than multiple sources operating at different wavelengths, to excite and discern different fluorescent molecules emitting in a same wavelength region can be less complex to operate and maintain, more compact, and may be manufactured at lower cost.

Although analytic systems based on fluorescent lifetime analysis may have certain benefits, the amount of information obtained by an analytic system and/or detection accuracy may be increased by allowing for additional detection techniques. For example, some analytic systems 5-160 may additionally be configured to discern one or more properties of a sample based on fluorescent wavelength and/or fluorescent intensity.

Referring again to FIG. 5-4, according to some embodiments, different fluorescent lifetimes may be distinguished with a photodetector that is configured to time-bin fluorescent emission events following excitation of a fluorescent molecule. The time binning may occur during a single charge-accumulation cycle for the photodetector. A charge-accumulation cycle is an interval between read-out events during which photo-generated carriers are accumulated in bins of the time-binning photodetector. The concept of determining fluorescent lifetime by time-binning of emission events is introduced graphically in FIG. 5-5. At time $t_e$ just prior to $t_1$, a fluorescent molecule or ensemble of fluorescent molecules of a same type (e.g., the type corresponding to curve B of FIG. 5-4) is (are) excited by a short or ultrashort optical pulse. For a large ensemble of molecules, the intensity of emission may have a time profile similar to curve B, as depicted in FIG. 5-5.

For a single molecule or a small number of molecules, however, the emission of fluorescent photons occurs according to the statistics of curve B in FIG. 5-4, for this example. A time-binning photodetector 5-322 may accumulate carriers generated from emission events into discrete time bins (three indicated in FIG. 5-5) that are temporally resolved with respect to the excitation time of the fluorescent molecule(s). When a large number of emission events are summed, carriers accumulated in the time bins may approximate the decaying intensity curve shown in FIG. 5-5, and the binned signals can be used to distinguish between different fluorescent molecules or different environments in which a fluorescent molecule is located. Examples of time-binning photodetectors are described in U.S. patent application Ser. No. 14/821,656, filed Aug. 7, 2015, titled "INTEGRATED DEVICE FOR TEMPORAL BINNING OF RECEIVED PHOTONS," which is incorporated herein by reference in its entirety. Additional examples of time-binning photodetectors are described in U.S. patent application Ser. No. 15/852,571, filed Dec. 22, 2017, titled "INTEGRATED PHOTODETECTOR WITH DIRECT BINNING PIXEL," which is incorporated herein by reference in its entirety.

In some embodiments, a time-binning photodetector may generate charge carriers in a photon absorption/carrier generation region and directly transfer charge carriers to a charge carrier storage bin in a charge carrier storage region. Such a time-binning photodetector may be referred to as a "direct binning pixel." Examples of direct binning pixels are described in U.S. patent application Ser. No. 15/852,571, filed Dec. 22, 2017, titled "INTEGRATED PHOTODETECTOR WITH DIRECT BINNING PIXEL," which is incorporated herein by reference. For explanation purposes, a non-limiting embodiment of a time-binning photodetector is depicted in FIG. 5-6. As shown in FIG. 5-6, time-binning photodetector 5-950 includes photon absorption/carrier generation region 5-952, bins of charge carrier storage region 5-958, and readout circuitry 5-960 that reads out signals from the bins of charge carrier storage region 5-958. The bin to which a charge carrier is transferred is based on the time of arrival of a photon in photon absorption/carrier generation region 5-952 that produces the charge carrier. FIG. 5-6 shows an example of time-binning photodetector having two bins in charge carrier storage region 5-958: bin 0 and bin 1. In some instances, bin 0 may aggregate charge carriers received in one period following a trigger event (e.g., a pulse of excitation light), and bin 1 may aggregate charge carriers received in a later time period with respect to a trigger event. However, charge storage region 5-958 may have any number of bins, such as one bin, three bins, four bins, or more. Time-binning photodetector 5-950 may include electrodes 5-953, 5-955, and 5-956, which may be configured to apply voltages to establish potential gradients to direct charge carriers. Time-binning photodetector 5-950 may include rejection region 5-965, which may act as a drain or otherwise be configured to discard charge carriers produced in photon absorption/carrier generation region 5-952. A period of time when charge carriers are rejected by rejection region 5-965 may be timed to occur during a trigger event, such as an excitation light pulse.

Since an excitation light pulse may produce a number of unwanted charge carriers in photon absorption/carrier generation region 5-952, a potential gradient may be established in pixel 5-950 to drain such charge carriers to rejection region 5-965 during a rejection period. As an example, rejection region 5-965 may include a high potential diffusion area where electrons are drained to a supply voltage. Rejection region 5-965 may include an electrode 5-956 that charge couples region 5-952 directly to rejection region 5-965. The voltage of the electrode 5-956 may be varied to establish a desired potential gradient in photon absorption/carrier generation region 5-952. During a rejection period, the voltage of the electrode 5-956 may be set to a level that draws carriers from the photon absorption/carrier generation region 5-952 into the electrode 5-956, and out to the supply voltage. For example, the voltage of the electrode 5-956 may be set to a positive voltage to attract electrons, such that they are drawn away from the photon absorption/carrier generation region 5-952 to rejection region 5-965. Rejection region 5-965 may be considered a "lateral rejection region" because it allows transferring carriers laterally from region 5-952 to a drain.

Following the rejection period, a photogenerated charge carrier produced in photon absorption/carrier generation region 5-952 may be time-binned. Individual charge carriers may be directed to a bin based on their time of arrival. To do so, the electrical potential between photon absorption/carrier generation region 5-952 and charge carrier storage region 5-958 may be changed in respective time periods to establish a potential gradient that causes the photogenerated charge carriers to be directed to respective time bins. For example, during a first time period a barrier 5-962 formed by electrode 5-953 may be lowered, and a potential gradient may be established from photon absorption/carrier generation region 5-952 to bin 0, such that a carrier generated during this period is transferred to bin 0. Then, during a second time period, a barrier 5-964 formed by electrode 5-955 may be lowered, and a potential gradient may be established from photon absorption/carrier generation region 5-952 to bin 1, such that a carrier generated during this later period is transferred to bin 1.

In some implementations, only a single photon on average may be emitted from a fluorophore following an excitation event, as depicted in FIG. 5-7A. After a first excitation event at time $t_{e1}$, the emitted photon at time may occur within a first time interval, so that the resulting electron signal is accumulated in the first electron-storage bin (contributes to bin 1). In a subsequent excitation event at time $t_{e2}$, the emitted photon at time to may occur within a second time interval, so that the resulting electron signal contributes to bin 2.

After a large number of excitation events and signal accumulations, the electron-storage bins of the time-binning photodetector 5-322 may be read out to provide a multi-valued signal (e.g., a histogram of two or more values, an N-dimensional vector, etc.) for a sample well. The signal values for each bin may depend upon the decay rate of the fluorophore. For example and referring again to FIG. 5-4, a fluorophore having a decay curve B will have a higher ratio of signal in bin 1 to bin 2 than a fluorophore having a decay curve A. The values from the bins may be analyzed and compared against calibration values, and/or each other, to determine the particular fluorophore, which in turn identifies the nucleotide or nucleotide analog (or any other molecule or sample of interest) linked to the fluorophore when in the sample well.

To further aid in understanding the signal analysis, the accumulated, multi-bin values may be plotted as a histogram, as depicted in FIG. 5-7B for example, or may be recorded as a vector or location in N-dimensional space. Calibration runs may be performed separately to acquire calibration values for the multi-valued signals (e.g., calibration histograms) for four different fluorophores linked to the four nucleotides or nucleotide analogs. As an example, the calibration histograms may appear as depicted in FIG. 5-8A (fluorescent label associated with the T nucleotide), FIG. 5-8B (fluorescent label associated with the A nucleotide), FIG. 5-8C (fluorescent label associated with the C nucleotide), and FIG. 5-8D (fluorescent label associated with the G nucleotide). A comparison of the measured multi-valued signal (corresponding to the histogram of FIG. 5-7B) to the calibration multi-valued signals may determine the identity "T" (FIG. 5-8A) of the nucleotide or nucleotide analog being incorporated into the growing strand of DNA.

In some implementations, fluorescent intensity may be used additionally or alternatively to distinguish between different fluorophores. For example, some fluorophores may emit at significantly different intensities or have a significant difference in their probabilities of excitation (e.g., at least a difference of about 35%) even though their decay rates may be similar. By referencing binned signals (bins 1-3) to measured excitation light bin 0, it may be possible to distinguish different fluorophores based on intensity levels.

In some embodiments, different numbers of fluorophores of the same type may be linked to different nucleotides or nucleotide analogs, so that the nucleotides may be identified based on fluorophore intensity. For example, two fluorophores may be linked to a first nucleotide (e.g., "C") or nucleotide analog and four or more fluorophores may be linked to a second nucleotide (e.g., "T") or nucleotide analog. Because of the different numbers of fluorophores, there may be different excitation and fluorophore emission probabilities associated with the different nucleotides. For example, there may be more emission events for the "T" nucleotide or nucleotide analog during a signal accumulation interval, so that the apparent intensity of the bins is significantly higher than for the "C" nucleotide or nucleotide analog.

The inventors have recognized and appreciated that distinguishing nucleotides or any other biological or chemical samples based on fluorophore decay rates and/or fluorophore intensities enables a simplification of the optical excitation and detection systems in an instrument 5-104. For example, optical excitation may be performed with a single-wavelength source (e.g., a source producing one characteristic wavelength rather than multiple sources or a source operating at multiple different characteristic wavelengths). Additionally, wavelength discriminating optics and filters may not be needed in the detection system. Also, a single photodetector may be used for each sample well to detect emission from different fluorophores.

The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

The inventors have recognized and appreciated that fluorophores having emission wavelengths in a range between about 560 nm and about 900 nm can provide adequate amounts of fluorescence to be detected by a time-binning photodetector (which may be fabricated on a silicon wafer using CMOS processes). These fluorophores can be linked to biological molecules of interest such as nucleotides or nucleotide analogs. Fluorescent emission in this wavelength range may be detected with higher responsivity in a silicon-based photodetector than fluorescence at longer wavelengths. Additionally, fluorophores and associated linkers in this wavelength range may not interfere with incorporation of the nucleotides or nucleotide analogs into growing strands of DNA. The inventors have also recognized and appreciated that fluorophores having emission wavelengths in a range between about 560 nm and about 660 nm may be optically excited with a single-wavelength source. An example fluorophore in this range is Alexa Fluor 647, available from Thermo Fisher Scientific Inc. of Waltham, Massachusetts. The inventors have also recognized and appreciated that excitation light at shorter wavelengths (e.g., between about 500 nm and about 650 nm) may be required to excite fluorophores that emit at wavelengths between about 560 nm and about 900 nm. In some embodiments, the time-binning photodetectors may efficiently detect longer-wavelength emission from the samples, e.g., by incorporating other materials, such as Ge, into the photodetectors active region.

In some embodiments, a sample may be labeled with one or more markers, and emission associated with the markers is discernable by the instrument. For example, the photodetector may be configured to convert photons from the emission light into electrons to form an electrical signal that may be used to discern a lifetime that is dependent on the emission light from a specific marker. By using markers with different lifetimes to label samples, specific samples may be identified based on the resulting electrical signal detected by the photodetector.

A sample may contain multiple types of molecules and different luminescent markers may uniquely associate with a molecule type. During or after excitation, the luminescent marker may emit emission light. One or more properties of the emission light may be used to identify one or more types of molecules in the sample. Properties of the emission light used to distinguish among types of molecules may include a fluorescence lifetime value, intensity, and/or emission wavelength. A photodetector may detect photons, including photons of emission light, and provide electrical signals indicative of one or more of these properties. In some embodiments, electrical signals from a photodetector may provide information about a distribution of photon arrival times across one or more time intervals. The distribution of photon arrival times may correspond to when a photon is detected after a pulse of excitation light is emitted by an excitation source. A value for a time interval may correspond to a number of photons detected during the time interval. Relative values across multiple time intervals may provide an indication of a temporal characteristic of the emission light (e.g., lifetime). Analyzing a sample may include distinguishing among markers by comparing values for two or more different time intervals within a distribution. In some embodiments, an indication of the intensity may be provided by determining a number of photons across all time bins in a distribution.

IV. Conclusion

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. A system comprising:
   an array of reaction chambers;
   first and second waveguides configured to deliver excitation light to at least a portion of the array of the reaction chambers; and
   a dummy structure disposed between the first and second waveguides, wherein:
     a vertical extent of an optical mode of the first waveguide is modulated to adjust confinement of light within, and along a length of, the first waveguide; and
     the dummy structure extends in parallel to the first waveguide along the length of the first waveguide.

2. The system of claim 1, wherein the vertical extent of the optical mode is modulated by changing a thickness of a waveguide core layer along the length of the waveguide.

3. The system of claim 1, wherein the vertical extent of the optical mode is modulated by changing a refractive index of a waveguide core or cladding material along the length of the waveguide.

4. The system of claim 2, wherein the thickness of the waveguide core layer along the length of the waveguide is changed by transferring a topography of a photoresist layer.

5. The system of claim 1, comprising:
   a plurality of waveguides having uniform widths; and
   a plurality of dummy structures having tapered widths,
   wherein the plurality of waveguides and the plurality of dummy structures are disposed alternatively.

6. The system of claim 5, wherein the plurality of waveguides and the plurality of dummy structures are in a waveguide core layer.

7. A system comprising:
   an array of reaction chambers;
   first and second waveguides configured to deliver excitation light to at least a portion of the array of the reaction chambers; and
   a dummy structure disposed between the first and second waveguides, wherein:
     a distance between the first waveguide and the reaction chambers is modulated to compensate for waveguide losses; and
     the dummy structure extends in parallel to the first waveguide along a length of the first waveguide.

8. The system of claim 7, wherein a thickness of a cladding layer of the waveguide is controlled to modulate the distance between the waveguide and the reaction chambers.

9. The system of claim 7, comprising:
   a plurality of waveguides having uniform widths; and
   a plurality of dummy structures having tapered widths,
   wherein the plurality of waveguides and the plurality of dummy structures are disposed alternatively.

10. The system of claim 7, comprising:
    a plurality of waveguides having tapered widths; and
    a plurality of dummy structures having tapered widths,
    wherein the plurality of waveguides and the plurality of dummy structures are disposed alternatively.

11. The system of claim 7, comprising:
    a plurality of waveguides having tapered widths in a first direction; and
    a plurality of dummy structures having tapered widths in a second direction opposite to the first direction,
    wherein the plurality of waveguides and the plurality of dummy structures are disposed alternatively.

12. A method comprising:
    providing first and second waveguides to deliver excitation light to an array of reaction chambers;
    providing a dummy structure between the first and second waveguides; and
    modulating a vertical extent of an optical mode of the first waveguide to adjust confinement of light within, and along a length of, the first waveguide,
    wherein the dummy structure extends in parallel to the first waveguide along the length of the first waveguide.

13. The method of claim 12, wherein the modulating includes changing a thickness of a waveguide core layer along the length of the waveguide.

14. The method of claim 12, wherein the modulating includes changing a refractive index of a waveguide core or cladding material.

15. A method comprising:
    providing first and second waveguides to deliver excitation light to an array of reaction chambers;
    providing a dummy structure between the first and second waveguides; and
    modulating a distance between the first waveguide and the reaction chambers to compensate for waveguide losses,
    wherein the dummy structure extends in parallel to the first waveguide along a length of the waveguide.

16. The method of claim 15, wherein the modulating includes controlling a thickness of a cladding layer of the waveguide.

17. The method of claim 16, wherein controlling the thickness of the cladding layer of the waveguide includes providing the cladding layer with a tapered thickness by planarizing a material for the cladding layer on a modulated waveguide pattern.

18. The method of claim 17, wherein controlling the thickness of the cladding layer of the waveguide includes providing the cladding layer with a tapered thickness by depositing a material for the cladding layer on a modulated waveguide pattern.

19. The method of claim 17, wherein controlling the thickness of the cladding layer of the waveguide includes providing the cladding layer with a tapered thickness by transferring a topography of a photoresist layer to the cladding layer.

20. A method comprising:
    forming an array of reaction chambers;
    forming first and second waveguides to deliver excitation light to the reaction chambers;
    forming a dummy structure between the first and second waveguides; and
    modulating the first and second waveguides to deliver as close to an equal amount of excitation light to each reaction chamber,
    wherein the dummy structure extends in parallel to the first waveguide along a length of the first waveguide.

21. The method as claimed in claim 20, wherein the modulating includes modulating a vertical extent of an optical mode of the waveguide.

22. The method as claimed in claim 20, wherein the modulating includes modulating a thickness along its length of the waveguide.

23. The method as claimed in claim 20, wherein the modulating includes modulating a distance along its length of the waveguide from each reaction chamber.

24. A method comprising:
exciting with excitation light delivered through first and second waveguides a sample within each of a plurality of reaction chambers,
wherein the waveguide is modulated such that a substantially same amount of light is delivered to each reaction chamber; and
wherein a dummy structure is disposed between the first and second waveguides and extends in parallel to the first waveguide along a length of the first waveguide.

* * * * *